United States Patent
Michiels et al.

(10) Patent No.: US 6,372,960 B1
(45) Date of Patent: Apr. 16, 2002

(54) BARSTAR GENE

(75) Inventors: Frank Michiels, Bottelare (BE); Mark Williams, Newark, DE (US)

(73) Assignee: Plant Genetic Systems, N.V., Gent (BE)

(*) Notice: Subject to any disclaimer, the term of this patent is extended or adjusted under 35 U.S.C. 154(b) by 0 days.

(21) Appl. No.: 09/068,101

(22) PCT Filed: Sep. 1, 1997

(86) PCT No.: PCT/EP97/04739

§ 371 Date: Aug. 26, 1998

§ 102(e) Date: Aug. 26, 1998

(87) PCT Pub. No.: WO98/10081

PCT Pub. Date: Mar. 12, 1998

(30) Foreign Application Priority Data

Sep. 3, 1996 (EP) ............................................. 96202446

(51) Int. Cl.[7] ........................ C12N 15/31; C12N 15/82; C12N 5/04; A01H 1/02; A01H 5/00

(52) U.S. Cl. ...................... 800/274; 800/278; 800/287; 800/288; 800/303; 800/306; 800/314; 800/320.1; 800/320.2; 800/320.3; 536/23.7; 435/199; 435/419; 435/468

(58) Field of Search .............................. 536/23.7, 24.1; 435/199, 419, 468; 800/274, 278, 287, 288, 303, 306, 314, 320.1, 320.2, 320.3

(56) References Cited

U.S. PATENT DOCUMENTS 5,380,831 A * 1/1995 Adang et al. ............ 536/23.71

FOREIGN PATENT DOCUMENTS

| EP | 0359472 A2 | 3/1990 |
|----|------------|--------|
| EP | 0412911 A1 | 2/1991 |
| WO | WO9002189 A1 | 3/1990 |
| WO | WO9213956 A1 | 8/1992 |
| WO | WO9213957 A1 | 8/1992 |
| WO | WO9325695 A1 | 12/1993 |

OTHER PUBLICATIONS

Varshaveky, Alexander, Cell, vol. 69 (1992) pp. 725–735.

H.A. Lutcke et al., *The Embo Journal,* vol. 6, No. 1, pp. 43–48, (1987).

M.G. Koziel et al., *Bio/Technology,* vol. 11, pp. 194–200 (Feb. 1993).

R.W. Hartley, *TIBS,* vol. 14, pp. 450–454, (Nov. 1989).

R.W. Hartley, *Biochemistry,* vol. 32, pp. 5978–5984, (1993).

* cited by examiner

*Primary Examiner*—David T. Fox
(74) *Attorney, Agent, or Firm*—Birch, Stewart, Kolasch & Birch, LLP

(57) ABSTRACT

Improved barstar DNAs, such as synthetic barstar DNAs, produce high amounts of barstar protein in eucaryotic cells, particularly in plant cells, and especially in stamen cells such as tapetum cells. Synthetic barstar DNAs have less than 40% A and T nucleotides. Other improved barstar DNAs encode improved barstar proteins which have an N-terminus which starts with Met-Xaa wherein Xaa is Alanine, Valine, Glycine, Aspartic acid or Glutamic acid. Plan cells and plants contain the improved barstar DNAs and/or express the improved barstar protein.

21 Claims, No Drawings

SEQUENCE LISTING

<160> NUMBER OF SEQ ID NOS: 10

<210> SEQ ID NO 1
<211> LENGTH: 270
<212> TYPE: DNA
<213> ORGANISM: Bacillus amyloliquefaciens
<220> FEATURE:
<221> NAME/KEY: misc_feature
<222> LOCATION: (1)..(270)
<223> OTHER INFORMATION: CDS, function = "inhibitor of barnase",
      product = "barstar"

<400> SEQUENCE: 1
atgaaaaaag cagtcattaa cggggaacaa atcagaagta tcagcgacct ccaccagaca      60
ttgaaaaagg agcttgccct tccggaatac tacggtgaaa acctggacgc tttatgggat     120
tgtctgaccg gatgggtgga gtacccgctc gttttggaat ggaggcagtt tgaacaaagc     180
aagcagctga ctgaaaatgg cgccgagagt gtgcttcagg ttttccgtga agcgaaagcg     240
gaaggctgcg acatcaccat catactttct                                      270

<210> SEQ ID NO 2
<211> LENGTH: 90
<212> TYPE: PRT
<213> ORGANISM: Artificial Sequence
<220> FEATURE:
<223> OTHER INFORMATION: Description of Artificial Sequence: protein

<400> SEQUENCE: 2

Met Lys Lys Ala Val Ile Asn Gly Glu Gln Ile Arg Ser Ile Ser Asp
 1               5                  10                  15

Leu His Gln Thr Leu Lys Lys Glu Leu Ala Leu Pro Glu Tyr Tyr Gly
            20                  25                  30

Glu Asn Leu Asp Ala Leu Trp Asp Cys Leu Thr Gly Trp Val Glu Tyr
        35                  40                  45

Pro Leu Val Leu Glu Trp Arg Gln Phe Glu Gln Ser Lys Gln Leu Thr
    50                  55                  60

Glu Asn Gly Ala Glu Ser Val Leu Gln Val Phe Arg Glu Ala Lys Ala
65                  70                  75                  80

Glu Gly Cys Asp Ile Thr Ile Ile Leu Ser
                85                  90

<210> SEQ ID NO 3
<211> LENGTH: 273
<212> TYPE: DNA
<213> ORGANISM: Artificial Sequence
<220> FEATURE:
<223> OTHER INFORMATION: Description of Artificial Sequence: other
      nucleic acid, "improved barstar DNA"
<220> FEATURE:
<221> NAME/KEY: misc_feature
<222> LOCATION: (1)..(273)
<223> OTHER INFORMATION: CDS

<400> SEQUENCE: 3
atggccaaga aggctgtcat caacggggag cagatcagga gcatcagcga cctccaccag      60
accctcaaga aggagcttgc ccttccggag tactacggtg agaacctcga cgccctctgg     120
gactgcctca ccggctgggt ggagtacccc ctcgtgttgg agtggaggca gttcgagcag     180
agcaagcagc tcaccgagaa cggcgccgag agcgtgctcc aagtgttcag ggaggccaag     240
gccgagggct gcgacatcac catcatcctc tcc                                  273

<210> SEQ ID NO 4
<211> LENGTH: 91
<212> TYPE: PRT
<213> ORGANISM: Artificial Sequence
<220> FEATURE:
<223> OTHER INFORMATION: Description of Artificial Sequence: protein

<400> SEQUENCE: 4

```
Met Ala Lys Lys Ala Val Ile Asn Gly Glu Gln Ile Arg Ser Ile Ser
 1               5                  10                  15

Asp Leu His Gln Thr Leu Lys Lys Glu Leu Ala Leu Pro Glu Tyr Tyr
            20                  25                  30

Gly Glu Asn Leu Asp Ala Leu Trp Asp Cys Leu Thr Gly Trp Val Glu
        35                  40                  45

Tyr Pro Leu Val Leu Glu Trp Arg Gln Phe Glu Gln Ser Lys Gln Leu
    50                  55                  60

Thr Glu Asn Gly Ala Glu Ser Val Leu Gln Val Phe Arg Glu Ala Lys
65                  70                  75                  80

Ala Glu Gly Cys Asp Ile Thr Ile Ile Leu Ser
                85                  90
```

<210> SEQ ID NO 5
<211> LENGTH: 4032
<212> TYPE: DNA
<213> ORGANISM: Artificial Sequence
<220> FEATURE:
<223> OTHER INFORMATION: Description of Artificial Sequence: other nucleic acid, "plasmid pMV71"
<220> FEATURE:
<221> NAME/KEY: misc_feature
<222> LOCATION: (1999)..(3400)
<223> OTHER INFORMATION: label = PRAC1, "promoter region of rice actin gene - contains an intron in the leader"
<220> FEATURE:
<221> NAME/KEY: misc_feature
<222> LOCATION: (3401)..(3676)
<223> OTHER INFORMATION: label = barstar, "barstar DNA"
<220> FEATURE:
<221> NAME/KEY: misc_feature
<222> LOCATION: (3677)..(4003)
<223> OTHER INFORMATION: label = 3'nos, "region containing 3' untranslated end of nopaline synthase gene of Agrobacterium T-DNA"
<220> FEATURE:
<221> NAME/KEY: misc_feature
<222> LOCATION: (3399)..(3404)
<223> OTHER INFORMATION: label = NcoI, "NcoI recognition site"
<220> FEATURE:
<221> NAME/KEY: misc_feature
<222> LOCATION: (4016)..(4021)
<223> OTHER INFORMATION: label = KpnI, "KpnI recognition site"

<400> SEQUENCE: 5

```
caagcttgac gtcaggtggc acttttcggg gaaatgtgcg cggaacccct atttgtttat      60
ttttctaaat acattcaaat atgtatccgc tcatgagaca ataaccctga taaatgcttc     120
aataatattg aaaaaggaag agtatgagta ttcaacattt ccgtgtcgcc cttattccct     180
tttttgcggc attttgcctt cctgtttttg ctcacccaga aacgctggtg aaagtaaaag     240
atgctgaaga tcagttgggt gcacgagtgg gttacatcga actggatctc aacagcggta     300
agatccttga gagttttcgc cccgaagaac gttttccaat gatgagcact tttaaagttc     360
tgctatgtgg cgcggtatta tcccgtattg acgccgggca agagcaactc ggtcgccgca     420
tacactattc tcagaatgac ttggttgagt actcaccagt cacagaaaag catcttacgg     480
```

-continued

```
atggcatgac agtaagagaa ttatgcagtg ctgccataac catgagtgat aacactgcgg      540
ccaacttact tctgacaacg atcggaggac cgaaggagct aaccgctttt ttgcacaaca      600
tgggggatca tgtaactcgc cttgatcgtt gggaaccgga gctgaatgaa gccataccaa      660
acgacgagcg tgacaccacg atgcctgtag caatggcaac aacgttgcgc aaactattaa      720
ctggcgaact acttactcta gcttcccggc aacaattaat agactggatg gaggcggata      780
aagttgcagg accacttctg cgctcggccc ttccggctgg ctggtttatt gctgataaat      840
ctggagccgt gagcgtggg tctcgcggta tcattgcagc actggggcca gatggtaagc      900
cctcccgtat cgtagttatc tacacgacgg ggagtcaggc aactatggat gaacgaaata      960
gacagatcgc tgagataggt gcctcactga ttaagcattg gtaactgtca gaccaagttt     1020
actcatatat actttagatt gatttaaaac ttcatttta atttaaaagg atctaggtga     1080
agatcctttt tggctcgagt ctcatgacca aatcccctta acgtgagttt tcgttccact     1140
gagcgtcaga ccccgtagaa aagatcaaag gatcttcttg agatcctttt tttctgcgcg     1200
taatctgctg cttgcaaaca aaaaaaccac cgctaccagc ggtggtttgt ttgccggatc     1260
aagagctacc aactctttt ccgaaggtaa ctggcttcag cagagcgcag ataccaaata     1320
ctgtccttct agtgtagccg tagttaggcc accacttcaa gaactctgta gcaccgccta     1380
catacctcgc tctgctaatc ctgttaccag tggctgctgc cagtggcgat aagtcgtgtc     1440
ttaccgggtt ggactcaaga cgatagttac cggataaggc gcagcggtcg ggctgaacgg     1500
ggggttcgtg cacacagccc agcttggagc gaacgaccta caccgaactg agatacctac     1560
agcgtgagca ttgagaaagc gccacgcttc ccgaagggag aaaggcggac aggtatccgg     1620
taagcggcag ggtcggaaca ggagagcgca cgagggagct tccaggggga aacgcctggt     1680
atctttatag tcctgtcggg tttcgccacc tctgacttga gcgtcgattt ttgtgatgct     1740
cgtcaggggg gcggagccta tggaaaaacg ccagcaacgc ggcctttta cggttcctgg     1800 ccttttgctg gccttttgct cacatgttct ttcctgcgtt atccctgat tctgtggata     1860 accgtattac cgcctttgag tgagctgata ccgctcgccg cagccgaacg accgagcgca     1920
gcgagtcagt gagcgaggaa gcggaagagc gcccaatacg caaaccgcct ctccccgcgc     1980
gttggcctga tcagaatttc gaggtcattc atatgcttga aagagagtc gggatagtcc     2040 aaaataaaac aaaggtaaga ttacctggtc aaaagtgaaa acatcagtta aaaggtggta     2100
taaagtaaaa tatcggtaat aaaaggtggc ccaaagtgaa atttactctt ttctactatt     2160
ataaaaattg aggatgtttt tgtcggtact ttgatacgtc attttttgtat gaattggttt     2220 ttaagtttat tcgcttttgg aaatgcatat ctgtatttga gtcgggtttt aagttcgttt     2280
gcttttgtaa atacagaggg atttgtataa gaaatatctt taaaaaaacc catatgctaa     2340
tttgacataa ttttttgagaa aaatatatat tcaggcgaat tctcacaatg aacaataata     2400
agattaaaat agctttcccc cgttgcagcg catgggtatt ttttctagta aaaataaaag     2460
ataaacttag actcaaaaca tttacaaaaa caacccctaa agttcctaaa gcccaaagtg     2520
ctatccacga tccatagcaa gcccagccca acccaaccca acccaaccca ccccagtcca     2580
gccaactgga caatagtctc cacacccccc cactatcacc gtgagttgtc cgcacgcacc     2640
gcacgtctcg cagccaaaaa aaaaaaaaga aagaaaaaaa agaaaagaa aaaacagcag     2700 gtgggtccgg gtcgtggggg ccggaaacgc gaggaggatc gcgagccagc gacgaggccg     2760
gccctccctc cgcttccaaa gaaacgcccc ccatcgccac tatatacata ccccccctc     2820 tcctcccatc cccccaaccc taccaccacc accaccacca cctccacctc ctccccctc     2880
```

```
gctgccggac gacgagctcc tccccctcc cctccgccg ccgccgcgcc ggtaaccacc    2940
ccgcccctct cctctttctt tctccgtttt tttttccgt ctcggtctcg atctttggcc    3000
ttggtagttt gggtgggcga gaggcggctt cgtgcgcgcc cagatcggtg cgcgggaggg    3060
gcgggatctc gcggctgggg ctctcgccgg cgtggatccg gcccggatct cgcggggaat    3120
ggggctctcg gatgtagatc tgcgatccgc cgttgttggg ggagatgatg ggggtttaa    3180 aatttccgcc atgctaaaca agatcaggaa gagggaaaa gggcactatg gtttatattt    3240
ttatatattt ctgctgcttc gtcaggctta gatgtgctag atctttcttt cttctttttg    3300
tgggtagaat ttgaatccct cagcattgtt catcggtagt ttttcttttc atgatttgtg    3360
acaaatgcag cctcgtgcgg agcttttttg taggtagacc atggccaaaa aagcagtcat    3420
taacggggaa caaatcagaa gtatcagcga cctccaccag acattgaaaa aggagcttgc    3480
ccttccggaa tactacggtg aaaacctgga cgctttatgg gattgtctga ccggatgggt    3540
ggagtacccg ctcgttttgg aatggaggca gtttgaacaa agcaagcagc tgactgaaaa    3600
tggcgccgag agtgtgcttc aggttttccg tgaagcgaaa gcggaaggct gcgacatcac    3660
catcatactt tcttaatacg atcaatggga gatgaacaat atggaaacac aaacccgcaa    3720
gctagcttgg ctctagagga tccgaagcag atcgttcaaa catttggcaa taaagtttct    3780
taagattgaa tcctgttgcc ggtcttgcga tgattatcat ataatttctg ttgaattacg    3840
ttaagcatgt aataattaac atgtaatgca tgacgttatt tatgagatgg gtttttatga    3900
ttagagtccc gcaattatac atttaatacg cgatagaaaa caaaatatag cgcgcaaact    3960
aggataaatt atcgcgcgcg gtgtcatcta tgttactaga tcgggaagat ccccgggtac    4020
cgagctcgaa tt                                                       4032
```

<210> SEQ ID NO 6
<211> LENGTH: 563
<212> TYPE: DNA
<213> ORGANISM: Artificial Sequence
<220> FEATURE:
<223> OTHER INFORMATION: Description of Artificial Sequence: other
      nucleic acid, "part of plasmid pLH43"
<220> FEATURE:
<221> NAME/KEY: misc_feature
<222> LOCATION: (1)..(6)
<223> OTHER INFORMATION: label = NcoI, "NcoI recognition site"
<220> FEATURE:
<221> NAME/KEY: misc_feature
<222> LOCATION: (3)..(278)
<223> OTHER INFORMATION: label = synb*, "improved barstar DNA"
<220> FEATURE:
<221> NAME/KEY: misc_feature
<222> LOCATION: (279)..(545)
<223> OTHER INFORMATION: label = 3'nos, "region containing 3'
      untranslated end of nopaline synthase gene of Agrobacterium
      T-DNA"
<220> FEATURE:
<221> NAME/KEY: misc_feature
<222> LOCATION: (558)..(563)
<223> OTHER INFORMATION: label = KpnI, "KpnI recognition site"

<400> SEQUENCE: 6

```
ccatggccaa gaaggctgtc atcaacgggg agcagatcag gagcatcagc gacctccacc      60
agaccctcaa gaaggagctt gcccttccgg agtactacgg tgagaacctc gacgccctct     120
gggactgcct caccggctgg gtggagtacc ccctcgtgtt ggagtggagg cagttcgagc     180
agagcaagca gctcaccgag aacggcgccg agagcgtgct ccaagtgttc agggaggcca     240
aggccgaggg ctgcgacatc accatcatcc tctcctgatg gatccgaagc agatcgttca     300
```

-continued

```
aacatttggc aataaagttt cttaagattg aatcctgttg ccggtcttgc gatgattatc    360
atataatttc tgttgaatta cgttaagcat gtaataatta acatgtaatg catgacgtta    420
tttatgagat gggtttttat gattagagtc ccgcaattat acatttaata cgcgatagaa    480
aacaaaatat agcgcgcaaa ctaggataaa ttatcgcgcg cggtgtcatc tatgttacta    540
gatcgggaag atccccgggt acc                                           563
```

<210> SEQ ID NO 7
<211> LENGTH: 5349
<212> TYPE: DNA
<213> ORGANISM: Artificial Sequence
<220> FEATURE:
<223> OTHER INFORMATION: Description of Artificial Sequence: other nucleic acid, "T-DNA of pTTS243"
<220> FEATURE:
<221> NAME/KEY: misc_feature
<222> LOCATION: Complement((1)..(25))
<223> OTHER INFORMATION: label = RB, "T-DNA right border"
<220> FEATURE:
<221> NAME/KEY: misc_feature
<222> LOCATION: Complement((98)..(331))
<223> OTHER INFORMATION: label = 3'g7, "region containing 3' untranslated end of Agrobacterium T-DNA gene 7"
<220> FEATURE:
<221> NAME/KEY: misc_feature
<222> LOCATION: Complement((332)..(883))
<223> OTHER INFORMATION: label = bar, "region coding for phosphinthricin acetyl transferase"
<220> FEATURE:
<221> NAME/KEY: misc_feature
<222> LOCATION: Complement((884)..(2258))
<223> OTHER INFORMATION: label = P35S, "35S promoter of Cauliflower Mosaic Virus"
<220> FEATURE:
<221> NAME/KEY: misc_feature
<222> LOCATION: (2281)..(3969)
<223> OTHER INFORMATION: label = PE1, "promoter of E1 gene of rice (WO92/13956)"
<220> FEATURE:
<221> NAME/KEY: misc_feature
<222> LOCATION: (3970)..(4245)
<223> OTHER INFORMATION: label = synb*; "improved barstar DNA"
<220> FEATURE:
<221> NAME/KEY: misc_feature
<222> LOCATION: (4246)..(4577)
<223> OTHER INFORMATION: label = 3'chs, "region containing 3' untranslated end of chalcone synthase gene"
<220> FEATURE:
<221> NAME/KEY: misc_feature
<222> LOCATION: Complement((5325)..(5349))
<223> OTHER INFORMATION: label = LB, "T-DNA left border"

<400> SEQUENCE: 7

```
aattacaacg gtatatatcc tgccagtact cggccgtcga actcggccgt cgagtacatg     60
gtcgataaga aaggcaatt tgtagatgtt aattcccatc ttgaaagaaa tatagtttaa    120
atatttattg ataaaataac aagtcaggta ttatagtcca agcaaaaaca taaatttatt    180
gatgcaagtt taaattcaga aatatttcaa taactgatta tatcagctgg tacattgccg    240
tagatgaaag actgagtgcg atattatgtg taatacataa attgatgata tagctagctt    300
agctcatcgg gggatcctag aacgcgtgat ctcagatctc ggtgacgggc aggaccggac    360
ggggcggtac cggcaggctg aagtccagct gccagaaacc cacgtcatgc cagttcccgt    420
gcttgaagcc ggccgcccgc agcatgccgc gggggcata tccgagcgcc tcgtgcatgc    480
gcacgctcgg gtcgttgggc agcccgatga cagcgaccac gctcttgaag ccctgtgcct    540
ccagggactt cagcaggtgg gtgtagagcg tggagcccag tcccgtccgc tggtggcggg    600
```

| | |
|---|---|
| gggagacgta cacggtcgac tcggccgtcc agtcgtaggc gttgcgtgcc ttccaggggc | 660 |
| ccgcgtaggc gatgccggcg acctcgccgt ccacctcggc gacgagccag ggatagcgct | 720 |
| cccgcagacg gacgaggtcg tccgtccact cctgcggttc ctgcggctcg gtacggaagt | 780 |
| tgaccgtgct tgtctcgatg tagtggttga cgatggtgca gaccgccggc atgtccgcct | 840 |
| cggtggcacg gcggatgtcg gccgggcgtc gttctgggtc catggttata gagagagaga | 900 |
| tagatttata gagagagact ggtgatttca gcgtgtcctc tccaaatgaa atgaacttcc | 960 |
| ttatatagag gaagggtctt gcgaaggata gtgggattgt gcgtcatccc ttacgtcagt | 1020 |
| ggagatgtca catcaatcca cttgctttga agacgtggtt ggaacgtctt cttttccac | 1080 |
| gatgctcctc gtgggtgggg gtccatcttt ggaccactg tcggcagagg catcttgaat | 1140 |
| gatagccttt cctttatcgc aatgatggca tttgtaggag ccaccttcct tttctactgt | 1200 |
| cctttcgatg aagtgacaga tagctgggca atggaatccg aggaggtttc ccgaaattat | 1260 |
| cctttgttga aaagtctcaa tagcccttg tcttctgag actgtatctt tgacattttt | 1320 |
| ggagtagacc agagtgtcgt gctccaccat gttgacgaag attttcttct tgtcattgag | 1380 |
| tcgtaaaaga ctctgtatga actgttcgcc agtcttcacg gcgagttctg ttagatcctc | 1440 |
| gatttgaatc ttagactcca tgcatggcct tagattcagt aggaactacc ttttagaga | 1500 |
| ctccaatctc tattacttgc cttggtttat gaagcaagcc ttgaatcgtc catactggaa | 1560 |
| tagtacttct gatcttgaga atatgtctt tctctgtgtt cttgatgcaa ttagtcctga | 1620 |
| atcttttgac tgcatcttta accttcttgg gaaggtattt gatctcctgg agattgttac | 1680 |
| tcgggtagat cgtcttgatg agacctgctg cgtaggcctc tctaaccatc tgtgggtcag | 1740 |
| cattcttct gaaattgaag aggctaacct tctcattatc agtggtgaac atagtgtcgt | 1800 |
| caccttcacc ttcgaacttc cttcctagat cgtaaagata gaggaaatcg tccattgtaa | 1860 |
| tctccggggc aaaggagatc tcttttgggg ctggatcact gctgggcctt ttggttccta | 1920 |
| gcgtgagcca gtgggctttt tgctttggtg ggcttgttag ggccttagca aagctcttgg | 1980 |
| gcttgagttg agcttctcct ttggggatga agttcaacct gtctgtttgc tgacttgttg | 2040 |
| tgtacgcgtc agctgctgct cttgcctctg taatagtggc aaatttcttg tgtgcaactc | 2100 |
| cgggaacgcc gtttgttgcc gcctttgtac aaccccagtc atcgtatata ccggcatgtg | 2160 |
| gaccgttata cacaacgtag tagttgatat gagggtgttg aatacccgat tctgctctga | 2220 |
| gaggagcaac tgtgctgtta agctcagatt tttgtgggcc cgggcctagg ctagcggccg | 2280 |
| cagatccttc tgtgtgattg ttttattaaa atttaatatt tatctggaat acctaccaat | 2340 |
| atatagtaga cttgtcaagc tgcaagaact tccaatcgcc gacaatacca atagagatcc | 2400 |
| aaccaccta atatcataaa caatctgatt gttagtccag aactatattg agtagtgaac | 2460 |
| aacaatagca cattaacatt atgaggatta ttggctaact ctgcaattca atattctgat | 2520 |
| gcgtctaatc tggtcaattt tagcgctcca gaaagaattg cacaatcctt ggacaatgtt | 2580 |
| ggcactggaa ctgttgcatg tttttacatc tcttattaac gtagcaaagg agtagattat | 2640 |
| tatgtaccag gagaaatctc ttcagatcct ttccacatgc aatgtcgtaa agaacagata | 2700 |
| cagtgtacgt tagtttgtaa tggacggtca atgccatttc tctgaaggca tgttcagaga | 2760 |
| tgatgatttc tgggatcctt ggaggggccc tgaaattcgg aaacagttag ttgagttta | 2820 |
| gtacctaatg tcttgcgtta tactacgtga aatgccattt ctgtaagctg agttttctac | 2880 |
| catctccaca ggaaataaag ctaataccctg tccaagagtg gtgcggcatt tgaccaaatg | 2940 |
| aagatcacaa gcatggcaag aatggcaatc tggcaaagga gcggaattat attgtattct | 3000 |

-continued

```
actacatcga acaggaacca tatcaatgtt gccccagcaa ggaccccgc agataagttc    3060 ctgttcttcc acagcagaat atccgcaact gcatagctcc caacaatgaa atccaaaacc    3120
acatcggctc agagagaagt tatgataaaa ggcactaatt ctgaataatt tcctagaaag    3180
cgaataataa tagcacacct tgacctccac caagaagctt gtggatcgac ttgtgcccat    3240
gaaatggcat tctgacattc tggtcactgt cagaatctct cggaaaatga ggaggcatag    3300
cttcgtgtgt gtatgtgtgt gggatattac gctgctaaaa ctttgtgttt ctgatcgatc    3360
tggttagaga gcatcgtctt tataagcact taaaaatggt agtataatct ctcaaggagc    3420
ctatactgcc aaggaaagga tagcttggcc tgtggggatt gagccgttga agggaacaaa    3480
cgaatacagt taccttacca gatgtttgcc acgacatggg caacgtcatt gctagaccaa    3540
gaaggcaaga agcaaagttt agctgtcaaa aagatatgc tagaggcttt ccagaatatg    3600
ttctatctca gccagaccaa tgggggcaaa atttactact atttgccata cattaaccac    3660
gtaaaagtcc tacactcaac ctaactgttg aacggtcctg ttctggccaa cggtgagaat    3720
gcacctaatg gacgggacaa cacttctttc accgtgctac tgctacatcc tgtagacggt    3780
ggacgcgtga ggtgctttcg ccatgaccgt ccttggttgt tgcagtcact gcgcacgct    3840 tgcaccgtga ctcacctgcc acattgcccc cgccgtcgcc ggcgcctaca aaagccacac    3900
acgcacgccg gccacgataa cccatcctag catcccggtg tccagcaaga gatccatcaa    3960
gccgtcgcga tggccaagaa ggctgtcatc aacggggagc agatcaggag catcagcgac    4020
ctccaccaga ccctcaagaa ggagcttgcc cttccggagt actacggtga gaacctcgac    4080
gccctctggg actgcctcac cggctgggtg gagtaccccc tcgtgttgga gtggaggcag    4140
ttcgagcaga gcaagcagct caccgagaac ggcgccgaga gcgtgctcca gtgttcagg    4200 gaggccaagg ccgagggctg cgacatcacc atcatcctct cctgatggat ctggggccgc    4260
tctagaacta gtggatcccc cgggctgcag gtcgggttgg gttattttct tatttccgta    4320
ataaaaaagt ggacatggtt acctattatt gtgatgtgtg ctgcatgtga gctatattgg    4380
cgatttctct cttgtaacgc tttgtacttg taccgtttcg ttgtgatcat tgaaataaag    4440
gcctatataa aaataattta tgttatttgt tggtttatgt gtgtgttttt ttttttttt    4500 tttagtcaaa atatttaagt atttctatat aaatcttttg caagtttttt aagtcatgga    4560
ggagatgtta tgaattctgt aatatagtaa aaatattacg tgaaaaacca gaggatccgg    4620
ggaattccca gatccgccta cctttcacga gttgcgcagt ttgtctgcaa gactctatga    4680
gaagcagata agcgataagt ttgctcaaca tcttctcggg cataagtcgg acaccatggc    4740
atcacagtat cgtgatgaca gaggcaggga gtgggacaaa attgaaatca ataatgatt    4800 ttattttgac tgatagtgac ctgttcgttg caacaaattg ataagcaatg ctttttata    4860 atgccaactt agtataaaaa agcaggcttc atccggattc tctgagccca ccgtgttcac    4920
caccaccgtg gtgctgttac gtctggcttt cagctgaatg gtgcagttct gtaccggttt    4980
tcctgtgccg tctttcagga ctcctgaaat ctttactgcc atattcaccc cacaaaaaag    5040
cccaccggtt ccggcgggct gtcataacac tgtgttacct ggctaatcag aatttataac    5100
cgaccccaac gatgaatccg tcagtacgcc agtcgccact gccggagcct tcataagcaa    5160
tatcaacaac gacggacgct gccggattaa tctgtatacc tgcactccac gccactgagg    5220
tatgccgcat tgcactttcg tccctggcag tggtcgtctc tttcatatac ccgactctag    5280
aggatccccc gggtaccgag ctctccccag atctgcatgg agccatttac aattgaatat    5340
```

```
atcctgccg                                                             5349
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: other
      nucleic acid, "oligonucleotide CASOLX1"
<220> FEATURE:
<221> NAME/KEY: misc_feature
<222> LOCATION: (10)..(15)
<223> OTHER INFORMATION: label = KpnI, "KpnI recognition site"

<400> SEQUENCE: 8

```
cagcctgccg gtaccgcccc gtcc                                               24
```

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: other
      nucleic acid, "oligonucleotide CASOLX2"
<220> FEATURE:
<221> NAME/KEY: misc_feature
<222> LOCATION: (5)..(10)
<223> OTHER INFORMATION: label = AatII, "AatII recognition site"
<220> FEATURE:
<221> NAME/KEY: misc_feature
<222> LOCATION: (30)..(50)
<223> OTHER INFORMATION: label = 3'g7, "part of 3' untranslated end of
      Agrobacterium T-DNA gene 7"

<400> SEQUENCE: 9

```
ccccgacgtc aagcttgaat tcgcgatacg tacatggtcg ataagaaaag                   50
```

<210> SEQ ID NO 10
<211> LENGTH: 5611
<212> TYPE: DNA
<213> ORGANISM: Artificial Sequence
<220> FEATURE:
<223> OTHER INFORMATION: Description of Artificial Sequence: other
      nucleic acid, "plasmid pLH48"
<220> FEATURE:
<221> NAME/KEY: misc_feature
<222> LOCATION: Complement((39)..(317))
<223> OTHER INFORMATION: label = 3'nos, "region containing 3'
      untranslated end of nopaline synthase gene of Agrobacterium
      T-DNA"
<220> FEATURE:
<221> NAME/KEY: misc_feature
<222> LOCATION: Complement((318)..(869))
<223> OTHER INFORMATION: label = bar, "region coding for
      phosphinothricin acetyl transferase"
<220> FEATURE:
<221> NAME/KEY: misc_feature
<222> LOCATION: Complement((870)..(1702))
<223> OTHER INFORMATION: label = P35S, "35S promoter of Cauliflower
      Mosaic Virus"
<220> FEATURE:
<221> NAME/KEY: misc_feature
<222> LOCATION: (1740)..(2284)
<223> OTHER INFORMATION: label = PTA29, "promoter of TA29 gene of
      Nicotiana tabacum"
<220> FEATURE:
<221> NAME/KEY: misc_feature
<222> LOCATION: (2285)..(2560)
<223> OTHER INFORMATION: label = synb*, "improved barstar DNA"
<220> FEATURE:
<221> NAME/KEY: misc_feature
<222> LOCATION: (2561)..(2892)
<223> OTHER INFORMATION: label = 3'chs, "region containing  3'
      untranslated end of chalcone synthase gene"

<400> SEQUENCE: 10

```
agcttgcatg cctgcaggtc gactctagag gatcttcccg atctagtaac atagatgaca    60
ccgcgcgcga taatttatcc tagtttgcgc gctatatttt gttttctatc gcgtattaaa   120
tgtataattg cgggactcta atcataaaaa cccatctcat aaataacgtc atgcattaca   180
tgttaattat tacatgctta acgtaattca acagaaatta tatgataatc atcgcaagac   240
cggcaacagg attcaatctt aagaaacttt attgccaaat gtttgaacga tctgcttcgg   300
atcctagacg cgtgagatca gatctcggtg acgggcagga ccggacgggg cggtaccggc   360
aggctgaagt ccagctgcca gaaacccacg tcatgccagt tcccgtgctt gaagccggcc   420
gcccgcagca tgccgcgggg ggcatatccg agcgcctcgt gcatgcgcac gctcgggtcg   480
ttgggcagcc cgatgacagc gaccacgctc ttgaagccct gtgcctccag ggacttcagc   540
aggtgggtgt agagcgtgga gcccagtccc gtccgctggt ggcggggga gacgtacacg    600
gtcgactcgg ccgtccagtc gtaggcgttg cgtgccttcc aggggcccgc gtaggcgatg   660
ccggcgacct cgccgtccac ctcggcgacg agccagggat agcgctcccg cagacggacg   720
aggtcgtccg tccactcctg cggttcctgc ggctcggtac ggaagttgac cgtgcttgtc   780
tcgatgtagt ggttgacgat ggtgcagacc gccggcatgt ccgcctcggt ggcacggcgg   840
atgtcggccg ggcgtcgttc tgggtccatg gttatagaga gagagataga tttatagaga   900
gagactggtg atttcagcgt gtcctctcca aatgaaatga acttccttat atagaggaag   960
ggtcttgcga aggatagtgg gattgtgcgt catcccttac gtcagtggag atgtcacatc  1020
aatccacttg ctttgaagac gtggttggaa cgtcttcttt ttccacgatg ctcctcgtgg  1080
gtggggtcc atctttggga ccactgtcgg cagaggcatc ttgaatgata gcctttcctt  1140
tatcgcaatg atggcatttg taggagccac cttccttttc tactgtcctt tcgatgaagt  1200
gacagatagc tgggcaatgg aatccgagga ggtttcccga aattatcctt tgttgaaaag  1260
tctcaatagc cctttggtct tctgagactg tatcttgac attttggag tagaccagag  1320
tgtcgtgctc caccatgttg acgaagattt tcttcttgtc attgagtcgt aaaagactct  1380
gtatgaactg ttcgccagtc ttcacggcga gttctgttag atcctcgatt tgaatcttag  1440
actccatgca tggccttaga ttcagtagga actaccttt tagagactcc aatctctatt  1500
acttgccttg gttatgaag caagccttga atcgtccata ctggaatagt acttctgatc  1560
ttgagaaata tgtctttctc tgtgttcttg atgcaattag tcctgaatct tttgactgca  1620
tctttaacct tcttgggaag gtatttgatc tcctggagat tgttactcgg gtagatcgtc  1680
ttgatgagac ctgctgcgta ggagcttgca tgcctgcagg tcgactctag aggatccca  1740
tctagctaag tataactgga taatttgcat taacagattg aatatagtgc caaacaagaa  1800
gggacaattg acttgtcact ttatgaaaga tgattcaaac atgatttttt atgtactaat  1860
atatacatcc tactcgaatt aaagcgacat aggctcgaag tatgcacatt tagcaatgta  1920
aattaaatca gttttttgaat caagctaaaa gcagacttgc ataaggtggg tggctggact  1980
agaataaaca tcttctctag cacagcttca taatgtaatt tccataactg aaatcagggt  2040
gagacaaaat tttggtactt tttcctcaca ctaagtccat gtttgcaaca aattaataca  2100
tgaaacctta atgttaccct cagattagcc tgctactccc catttcctc gaaatgctcc  2160
aacaaaagtt agttttgcaa gttgttgtgt atgtcttgtg ctctatatat gcccttgtgg  2220
tgcaagtgta acagtacaac atcatcactc aaatcaaagt ttttacttaa agaaattagc  2280
```

-continued

| | |
|---|---|
| taccatggcc aagaaggctg tcatcaacgg ggagcagatc aggagcatca gcgacctcca | 2340 |
| ccagaccctc aagaaggagc ttgcccttcc ggagtactac ggtgagaacc tcgacgccct | 2400 |
| ctgggactgc ctcaccggct gggtggagta ccccctcgtg ttggagtgga ggcagttcga | 2460 |
| gcagagcaag cagctcaccg agaacggcgc cgagagcgtg ctccaagtgt tcagggaggc | 2520 |
| caaggccgag ggctgcgaca tcaccatcat cctctcctga tggatctggg gccgctctag | 2580 |
| aactagtgga tcccccgggc tgcaggtcgg gttgggttat tttcttattt ccgtaataaa | 2640 |
| aaagtggaca tggttaccta ttattgtgat gtgtgctgca tgtgagctat attggcgatt | 2700 |
| tctctcttgt aacgctttgt acttgtaccg tttcgttgtg atcattgaaa taaaggccta | 2760 |
| tataaaaata atttatgtta tttgttggtt tatgtgtgtg tttttttttt tttttttag | 2820 |
| tcaaaatatt taagtatttc tatataaatc ttttgcaagt tttttaagtc atggaggaga | 2880 |
| tgttatgaat tctgtaatat agtaaaaata ttacgtgaaa aaccagagga tccgggaat | 2940 |
| tcccagatcc gcctacctt cacgagttgc gcagtttgtc tgcaagactc tatgagaagc | 3000 |
| agataagcga taagtttgct caacatcttc tcgggcataa gtcggacacc atggcatcac | 3060 |
| agtatcgtga tgacagaggc agggagtggg acaaaattga aatcaaataa tgatttatt | 3120 |
| ttgactgata gtgacctgtt cgttgcaaca aattgataag caatgctttt ttataatgcc | 3180 |
| aacttagtat aaaaaagcag gcttcatccg gattctctga gcccaccgtg ttcaccacca | 3240 |
| ccgtggtgct gttacgtctg gctttcagct gaatggtgca gttctgtacc ggttttcctg | 3300 |
| tgccgtcttt caggactcct gaaatcttta ctgccatatt caccccacaa aaagcccac | 3360 |
| cggttccggc gggctgtcat aacactgtgt tacctggcta atcagaattt ataaccgacc | 3420 |
| ccaacgatga atccgtcagt acgccagtcg ccactgccgg agccttcata gcaaatatca | 3480 |
| acaacgacgg acgctgccgg attaatctgt atacctgcac tccacgccac tgaggtatgc | 3540 |
| cgcattgcac tttcgtccct ggcagtggtc gtctctttca tataccgac tctagaggat | 3600 |
| cccccgggta ccgagctcga attctgatca ggccaacgcg cggggagagg cggtttgcgt | 3660 |
| attgggcgct cttccgcttc ctcgctcact gactcgctgc gctcggtcgt tcggctgcgg | 3720 |
| cgagcggtat cagctcactc aaaggcggta atacggttat ccacagaatc aggggataac | 3780 |
| gcaggaaaga acatgtgagc aaaaggccag caaaaggcca ggaaccgtaa aaaggccgcg | 3840 |
| ttgctggcgt ttttccatag gctccgcccc cctgacgagc atcacaaaaa tcgacgctca | 3900 |
| agtcagaggt ggcgaaaccc gacaggacta taaagatacc aggcgtttcc ccctggaagc | 3960 |
| tccctcgtgc gctctcctgt tccgaccctg ccgcttaccg gatacctgtc cgcctttctc | 4020 |
| ccttcgggaa gcgtggcgct ttctcaatgc tcacgctgta ggtatctcag ttcggtgtag | 4080 |
| gtcgttcgct ccaagctggg ctgtgtgcac gaaccccccg ttcagcccga ccgctgcgcc | 4140 |
| ttatccggta actatcgtct tgagtccaac ccggtaagac acgacttatc gccactggca | 4200 |
| gcagccactg gtaacaggat tagcagagcg aggtatgtag gcggtgctac agagttcttg | 4260 |
| aagtggtggc ctaactacgg ctacactaga aggacagtat ttggtatctg cgctctgctg | 4320 |
| aagccagtta ccttcggaaa aagagttggt agctcttgat ccggcaaaca accaccgct | 4380 |
| ggtagcggtg ttttttgt ttgcaagcag cagattacgc gcagaaaaaa aggatctcaa | 4440 |
| gaagatcctt tgatcttttc tacggggtct gacgctcagt ggaacgaaaa ctcacgttaa | 4500 |
| gggattttgg tcatgagact cgagccaaaa aggatcttca cctagatcct ttaaattaa | 4560 |
| aaatgaagtt ttaaatcaat ctaaagtata tatgagtaaa cttggtctga cagttaccaa | 4620 |
| tgcttaatca gtgaggcacc tatctcagcg atctgtctat ttcgttcatc catagttgcc | 4680 |

```
tgactccccg tcgtgtagat aactacgata cgggagggct taccatctgg ccccagtgct    4740
gcaatgatac cgcgagaccc acgctcaccg gctccagatt tatcagcaat aaaccagcca    4800
gccggaaggg ccgagcgcag aagtggtcct gcaactttat ccgcctccat ccagtctatt    4860
aattgttgcc gggaagctag agtaagtagt tcgccagtta atagtttgcg caacgttgtt    4920
gccattgcta caggcatcgt ggtgtcacgc tcgtcgtttg gtatggcttc attcagctcc    4980
ggttcccaac gatcaaggcg agttacatga tcccccatgt tgtgcaaaaa agcggttagc    5040
tccttcggtc ctccgatcgt tgtcagaagt aagttggccg cagtgttatc actcatggtt    5100
atggcagcac tgcataattc tcttactgtc atgccatccg taagatgctt ttctgtgact    5160
ggtgagtact caaccaagtc attctgagaa tagtgtatgc ggcgaccgag ttgctcttgc    5220
ccggcgtcaa tacgggataa taccgcgcca catagcagaa ctttaaaagt gctcatcatt    5280
ggaaaacgtt cttcggggcg aaaactctca aggatcttac cgctgttgag atccagttcg    5340
atgtaaccca ctcgtgcacc caactgatct tcagcatctt ttactttcac cagcgtttct    5400
gggtgagcaa aaacaggaag gcaaaatgcc gcaaaaaagg gaataagggc gacacggaaa    5460
tgttgaatac tcatactctt ccttttcaa tattattgaa gcatttatca gggttattgt    5520
ctcatgagcg gatacatatt tgaatgtatt tagaaaaata aacaaatagg ggttccgcgc    5580
acatttcccc gaaaagtgcc acctgacgtc a                                   5611
```

BARSTAR GENE

This application claims the benefit under 35 U.S.C. §371 of prior PCT International Application No. PCT/EP97/04739, which has an International filing date of Sep. 1, 1997, which designated the United States of America, the entire contents of which are hereby incorporated by references.

The present invention relates to an improved barstar gene and improved barstar protein that can be used to neutralize the activity of a barnase in eucaryotic cells, particularly in plant cells. Thus the improved barstar gene can be used to produce fertility restorer plants capable of restoring the fertility to a line of male-sterile plants that contain in the nuclear genome of their cells a chimeric gene comprising a stamen-selective promoter and a DNA coding for a barnase. The present invention also relates to the restorer plants that contain in the nuclear genome of their cells the improved barstar gene.

BACKGROUND TO THE INVENTION

In many, if not most plant species, the development of hybrid cultivars is highly desired because of their generally increased productivity due to heterosis: the superiority of performance of hybrid individuals compared with their parents (see e.g. Fehr, 1987, Principles of cultivar development, Volume 1: Theory and Technique, MacMillan Publishing Company, New York; Allard, 1960, Principles of Plant Breeding, John Wiley and Sons, Inc.).

The development of hybrid cultivars of various plant species depends upon the capability to achieve almost complete cross-pollination between parents. This is most simply achieved by rendering one of the parent lines male sterile (i.e. bringing them in a condition so that pollen is absent or nonfunctional) either manually, by removing the anthers, or genetically by using, in the one parent, cytoplasmic or nuclear genes that prevent anther and/or pollen development (for a review of the genetics of male sterility in plants see Kaul, 1988, 'Male Sterility in Higher Plants', Springer Verlag).

For hybrid plants where the seed is the harvested product (e.g. corn, oilseed rape) it is in most cases also necessary to ensure that fertility of the hybrid plants is fully restored. In systems in which the male sterility is under genetic control this requires the existence and use of genes that can restore male fertility. The development of hybrid cultivars is mainly dependent on the availability of suitable and effective sterility and restorer genes.

Endogenous nuclear loci are known for most plant species that may contain genotypes which affect male sterility, and generally, such loci need to be homozygous for particular recessive alleles in order to result in a male-sterile phenotype. The presence of a dominant 'male fertile' allele at such loci results in male fertility.

Recently it has been shown that male sterility can be induced in a plant by providing the genome of the plant with a chimeric male-sterility gene comprising a DNA sequence (or male-sterility DNA) coding, for example, for a cytotoxic product (such as an RNase) and under the control of a promoter which is predominantly active in selected cells of the male reproductive organs. In this regard stamen-selective promoters, such as the promoter of the TA29 gene of *Nicotiana tabacum*, have been shown to be particularly useful for this purpose (Mariani et al., 1990, Nature 347:737, European patent publication ("EP") 0,344,029). By providing the nuclear genome of the plant with such a male-sterility gene, an artificial male-sterility locus is created containing the artificial male-sterility genotype that results in a male-sterile plant.

In addition it has been shown that male fertility can be restored to the plant with a chimeric fertility-restorer gene comprising another DNA sequence (or fertility-restorer DNA) that codes, for example, for a protein that inhibits the activity of the cytotoxic product or otherwise prevents the cytotoxic product to be active in the plant cells (European patent publication "EP" 0,412,911). For example the barnase gene of *Bacillus amyloliquefaciens* codes for an RNase, the barnase, which can be inhibited by a protein, the barstar, that is encoded by the barstar gene of *B. amyloliquefaciens*. The barnase gene can be used for the construction of a sterility gene while the barstar gene can be used for the construction of a fertility-restorer gene. Experiments in different plant species, e.g. oilseed rape, have shown that a chimeric barstar gene can fully restore the male fertility of male sterile lines in which the male sterility was due to the presence of a chimeric barnase gene (EP 0,412,911, Mariani et al., 1991, Proceedings of the CCIRC Rapeseed Congress, Jul. 9–11, 1991, Saskatoon, Saskatchewan, Canada; Mariani et al., 1992, Nature 357:384). By coupling a marker gene, such as a dominant herbicide resistance gene (for example the bar gene coding for phosphinothricin acetyl transferase (PAT) that converts the herbicidal phosphinothricin to a non-toxic compound [De Block et al., 1987, EMBO J. 6:2513]), to the chimeric male-sterility and/or fertility-restorer gene, breeding systems can be implemented to select for uniform populations of male sterile plants (EP 0,344,029; EP 0,412,911).

The production of hybrid seed of any particular cultivar of a plant species requires the: 1) maintenance of small quantities of pure seed of each inbred parent, and 2) the preparation of larger quantities of seed of each inbred parent. Such larger quantities of seed would normally be obtained by several (usually two) seed multiplication rounds, starting from a small quantity of pure seed ("basic seed") and leading, in each multiplication round, to a larger quantity of pure seed of the inbred parent and then finally to a stock of seed of the inbred parent (the "parent seed" or "foundation seed") which is of sufficient quantity to be planted to produce the desired quantities of hybrid seed. Of course, in each seed multiplication round larger planting areas (fields) are required.

Barnase is the ribonuclease which is secreted by *Bacillus amyloliquefaciens* and barstar is the inhibitor of barnase that is produced by the same microorganism (Hartley, 1988, J. Mol. Biol. 202:913–915). Several mutant barnase and barstar proteins have been described (Hartley, 1993, Biochemistry 32:5978–5984; Schreiber and Fersht, 1993, Biochemistry 32:5145–5150; Guillet et al, 1993, Current Biology 1:165–177; Hartley, 1989, TIBS 14:450–454; Axe et al, 1996, PNAS 93:5590–5594; Serrano, 1993, J. Mol. Biol. 233:305–312).

Some of these mutants were shown to essentially retain the biological activity of the barnase and barstar as produced by *Bacillus amyloliguefaciens*. However, at least two mutant barstars have been described that have no detectable barstar activity (Hartley, 1993, Biochemistry 32:5978–5984; Guillet et al, 1993, Current Biology 1 :165–177).

Also other related microorganisms are known to produce proteins that are highly similar to barnase and barstar. Thus *Bacillus intermedius* produces binase and binstar (Schulga et al, 1992, NAR 20:2375; Guillet et al, 1993, supra).

SUMMARY OF THE INVENTION

The present invention provides improved barstar DNAs that encode a barstar with an amino acid sequence that starts with Met-Xaa wherein Xaa is Alanine, Valine, Glycine, Aspartic acid or Glutamic acid. Preferably the barstar DNAs encode barstar having an amino acid sequence which is 1) the amino acid sequence of SEQ ID No 2 in which the second amino acid is not Lysine but is Alanine, Valine, Glycine, Aspartic acid or Glutamic acid; 2) the amino acid sequence of SEQ ID No 4; or the amino acid sequence of SEQ ID No 4 in which the second amino acid is not Alanine, but is Valine, Glycine, Aspartic acid or Glutamic acid.

The present invention further provides improved synthetic barstar DNAs that contain less than 40% A and T nucleotides and/or that have a codon usage that is optimized for oilseed rape, cotton, maize, rice and wheat, preferably for oilseed rape, maize and rice. Preferably the synthetic barstar DNAs contain no more than 7% CG dinucleotides and/or no more than 9.5% of CNG trinucleotides. A preferred synthetic barstar DNA encodes a barstar having the amino acid sequence of SEQ ID No. 4. A particularly preferred synthetic barstar DNA has the nucleotide sequence of SEQ ID No 3.

The present invention also provides: chimeric genes in which the improved barstar DNAs are operably linked to a plant expressible promoter, preferably a promoter that directs expression selectively in stamen cells and that directs expression at least in tapetum cells; plant cells and plants comprising these chimeric genes.

The present invention further provides uses of the improved barstar DNAs and imporved barstar proteins to neutralize barnases in plant cells, particularly with regard to restoration of male fertility to male-sterile lines.

The present invention also provides improved barstars having an amino acid sequence that starts with Met-Xaa where Xaa is Alanine, Valine, Glycine, Aspartic acid or Glutamic acid.

DETAILED DESCRIPTION OF THE INVENTION

A male-sterile ("ms") plant as used herein is a plant of a given plant species which is male-sterile due to expression of a chimeric male-sterility gene (S), integrated in the nuclear DNA of that plant and comprising the following operably linked DNA fragments:

1) A "sterility promoter" which directs expression selectively in stamen cells, and preferably at least in tapetum cells, and, 2) A "male-sterility DNA" coding for a barnase (the "barnase DNA").

An example of such a male-sterility gene is a gene comprising a barnase DNA under control of the promoter of the TA29 gene from tobacco, as for instance contained in plasmid pVE108 (WO 92/29696).

A restorer plant as used herein is a male-fertile plant of the same plant species that contains integrated in the nuclear DNA of its cells a fertility restorer gene (R) comprising:

1) A "restorer promoter" which directs expression at least in those stamen cells in which the sterility promoter directs expression of the barnase DNA in the ms plant, and, 2) A "restorer DNA" coding for a barstar (the "barstar DNA").

In the restorer plants of this invention the barstar DNA is the improved barstar DNA as described below.

The presence of the fertility restorer gene in those progeny plants of a male-sterile plant that contain the male-sterility gene, restores the male fertility in those progeny plants. The progeny plants are of course obtained from a cross between a male-sterile plant and the restorer plant.

A restored plant as used herein is a plant (of the same species as the male-sterile. plant and the restorer plant) that is male-fertile and that contains within its genome the male-sterility gene and the fertility-restorer gene, particularly the fertility restorer gene comprising the improved barstar DNA of this invention.

A line is the progeny of a given individual plant. The plants of a given line resemble each other in one or more particular genetic and/or phenotypic characteristics. As used herein a male-sterile (ms) line is a group of plants of a plant species, particularly of a plant variety, which are all male-sterile due to the presence of a particular male-sterility gene at the same genetic locus. Similarly, a restorer line is a group of plants of a plant species which all contain the particular fertility restorer gene at the same genetic locus. Preferably all the plants of a ms line (respectively a restorer line) have the same genotype with respect to the male-sterility locus (respectively the fertility restorer locus).

Male fertility is restored to a male-sterile line by introducing the fertility restorer gene in the ms line, e.g. by crossing of the plants of the ms line with plants of the restorer line so that at least some of the progeny plants will be restored plants.

The genetic background of a line of a variety designates the totality of genes present in the variety that determine the particular phenotypic characteristics of that variety. A foreign gene, such as a male-sterility gene or a restorer gene, introduced by genetic engineering to produce a particular line of a variety can thus be introduced in different varieties (or even in different species), each having a different genetic background.

For the production of hybrid seed the male-sterile line is also called the female or first parent line, and the male-fertile (restorer) line is also called the male or second parent line.

A gene as used herein is generally understood to comprise at least one coding region coding for an RNA, protein or polypeptide which is operably linked to suitable promoter and 3' regulatory sequences.

For the purpose of this invention the expression of a gene, such as a chimeric gene, will mean that the promoter of the gene directs transcription of a DNA into a RNA which is biologically active i.e. which is either capable of interacting with another RNA or protein, or which is capable of being translated into a biologically active polypeptide or protein.

The phenotype is the external appearance of the expression (or lack of expression) of a genotype i.e. of a gene or set of genes (e.g. male-sterility, presence of protein or RNA in specific plant tissues etc.).

A barnase as used herein is any protein which is capable of degrading single-stranded RNA and which comprises the amino acid sequence of barnase (secreted barnase) as secreted by *Bacillus amyloliquefaciens* (Hartley, 1988, J. Mol. Biol. 202:913) or an amino acid sequence having at least 80%, preferably at least 85% sequence identity with this sequence. Barnases, as used herein are capable of degrading RNA by a reaction which involves the initial cleaving of the phosphodiester bond between the 5' ribose of one nucleotide and the phosphate group attached to the neighbouring 3' nucleotide. The initial product of this reaction is a 2',3'-cyclic phosphate intermediate which is subsequently hydrolyzed to the corresponding 3' nucleoside phosphate. Barnases are also capable of hydrolyzing polyethenoadenosine phosphate to yield a highly fluorogenic nucleotide analogue 1,N-ethenoadenosine (Fitzgerald and Hartley, 1993, Anal. Biochem. 214:544–547) and have at least 10%, preferably at least 50%, particularly at least 75% of the activity of secreted barnase as measured under standard conditions (Fitzgerald and Hartley, 1993, Anal. Biochem. 214:544–547; Hartley, 1993, Biochemistry 32:5978:5984). Barnases are further capable of specific binding to wild-type barstar (see below) with a dissociation constant of $10^{-12}$ M or less, preferably with a dissociation constant of the order $10^{3113}$ M to $10^{-14}$ M (Schreiber and Fersht, 1993, Biochemistry 32:5145–5150; Hartley, 1993, Biochemistry 32:5978–5984).

Binase is the extracellular ribonuclease secreted by *Bacillus intermedius* (Schulga et al, 1992, NAR 20:2375) and is also considered to be a barnase as used in this invention.

For convenience barnase, as used in the description or in the Examples below, will designate a protein having the amino acid sequence of the barnase encoded by pVE108 (WO 92/09696).

A barstar is any protein that is capable of specific binding to secreted barnase with a dissociation constant of $10^{-12}$ M or less, preferably with a dissociation constant of the order of $10^{-13}$ M to $10^{-14}$ M (Schreiber and Fersht, 1993, Biochemistry 32:5145–5150; Hartley, 1993, Biochemistry 32:5978–5984). Barstars are capable of inhibiting at least 50%, particularly at least 75%, more particularly at least 90% of the activity of secreted barnase in an equimolar mixture of barstar and secreted barnase in standard conditions (Hartley, 1993, Biochemistry 32:5978–5984). A barstar is a protein comprising the amino acid sequence of SEQ ID No 2 or an amino acid sequence having at least 80%, preferably at least 85% sequence identity with this sequence. Wild type barstar is the barstar produced by *Bacillus amyloliquefaciens* and having the amino acid sequence of SEQ ID No 2 (see also Hartley, J. Mol. Biol. 1988 202:913). It goes without saying that barstars as used herein include for example the biologically active barstar mutants described by Hartley (1993, Biochemistry 32:5978–5984).

A barnase DNA (or barnase coding sequence) as used herein is any DNA fragment having a nucleotide sequence coding for a barnase. A particularly preferred barnase DNA is the barnase DNA as present in pVE108 (WO 92/09696). A barnase gene is a plant-expressible chimeric gene comprising a barnase DNA operably linked to suitable 5' and 3' regulatory regions, i.e. a promoter region comprising a promoter recognized by the polymerases of a plant cell and a 3' region comprising a plant polyadenylation site.

A barstar DNA (or barstar coding sequence) as used herein is any DNA fragment having a nucleotide sequence coding for a barstar. A wild type barstar DNA is the DNA which codes for wild-type barstar and which has the nucleotide sequence of SEQ ID No 1. (Hartley, J. Mol. Biol. 1988 202:913). A barstar gene is a plant-expressible chimeric gene comprising a barstar DNA operably linked to suitable 5' and 3' regulatory regions, i.e. a promoter region comprising a promoter recognized by the polymerases of a plant cell and a 3' region comprising a plant polyadenylation site.

As used herein, a genetic locus is the position of a given gene in the nuclear genome, i.e. in a particular chromosome, of a plant. Two loci can be on different chromosomes and will segregate independently. Two loci can be located on the same chromosome and are then generally considered as being linked (unless sufficient recombination can occur between them).

An endogenous locus is a locus which is naturally present in a plant. A foreign locus is a locus which is formed in the plant because of the introduction, by means of genetic transformation, of a foreign DNA.

In diploid plants, as in any other diploid organisms, two copies of a gene are present. at any autosomal locus. Any gene can be present in the nuclear genome in several variant states designated as alleles. If two identical alleles are present at a locus that locus is designated as being homozygous, if different alleles are present, the locus is designated as being heterozygous. The allelic composition of a locus, or a set of loci, is the genotype. Any allele at a locus is generally represented by a separate symbol (e.g. R and-, S and-, - representing the absence of the gene). A foreign locus is generally characterized by the presence and/or absence of a foreign DNA. A dominant allele is generally represented by a capital letter and is usually associated with the presence of a biologically active gene product (e.g. a protein) and an observable phenotypic effect (e.g. R indicates the production of an active barstar protein).

A plant can be genetically characterized by identification of the allelic state of at least one genetic locus.

The genotype of any given locus can be designated by the symbols for the two alleles that are present at the locus (e.g. R/R or S/-). The genotype of two unlinked loci can be represented as a sequence of the genotype of each locus (e.g. S/-,R/-)

A male sterile plant as used herein, contains a foreign "male-sterility locus" which contains the male-sterility gene S which when expressed in cells of the plant make the plant male-sterile without otherwise substantially affecting the growth and development of the plant.

The male-sterility locus preferably also comprises in the same genetic locus at least one first marker gene which comprises at least:

1) a first marker DNA encoding a first marker RNA, protein or polypeptide which, when present at least in a specific tissue or specific cells of the plant, renders the plant easily separable from other plants which do not contain the first marker RNA, protein or polypeptide encoded by the first marker DNA at least in the specific tissue or specific cells, and, 2) a first marker promoter capable of directing expression of the first marker DNA at least in the specific tissue or specific cells: the first marker DNA being in the same transcriptional unit as, and under the control of, the first marker promoter.

Such a male-sterility gene is always a dominant allele at such a foreign male-sterility locus. The recessive allele corresponds to the absence of the male-sterility gene in the nuclear genome of the plant.

Sterility promoters that can be used in the male-sterility genes in the first parent line of this invention have been described before (EP 0,344,029 and EP 0,412,911). The sterility promoter can be any promoter but it should at least be active in stamen cells, particularly tapetum cells. Particularly useful sterility promoters are promoters that are selectively active in stamen cells, such as the tapetum-specific promoters of the TA29 gene of *Nicotiana tabacum* (EP 0,344,029) which can be used in tobacco, oilseed rape, lettuce, cichory, corn, rice, wheat and other plant species; the PT72, the PT42 and PE1 promoters from rice which can be used in rice, corn, wheat, and other plant species (WO 92/13956); the PCA55 promoter from corn which can be used in corn, rice, wheat and other plant species (WO 92/13957); and the A9 promoter of a tapetum-specific gene of *Arabidopsis thaliana* (Wyatt et al., 1992, Plant Mol. Biol. 19:611–922).

The present invention is based on the finding that the "restorer capacity" (the ability and efficiency of a restorer line to restore male fertility efficiently to a wide variety of ms lines) is directly related to the amount of barstar produced in the stamen, particularly in the tapetum cells, of the restorer plants (and by implication in stamen, particularly the tapetum cells, of the restored plants).

Restorer capacity is important because an efficient restorer line can be used for the restoration of male fertility to a wide variety of male-sterile lines, which may differ in the level to which barnase is produced (by expression of the male-sterility gene) in the stamen, particularly in the tapetum cells. One source of such a variety of barnase production among different ms lines may be due to position effects, i.e. the variation in gene expression of the ms gene due to the different insertion places in the nuclear genome among different transformants. Another source of variation of barnase production among various ms lines that contain the ms gene at the same genetic locus is the different genetic backgrounds of the various ms lines. Thus when the ms gene from one male-sterile line of one variety of a plant species is introduced into other varieties of the same (or of a closely related) plant species by backcrossing to generate ms lines of those varieties the ms gene is introduced in a different genetic background which can influence the level at which the ms gene is expressed. The observed variation in barnase production, and the problems associated therewith with respect to fertility restoration, is further augmented when variation of expression of the restorer gene among different restorer plants is taken into account—such variation may originate from the same sources as indicated above, i.e. position effects of the fertility restorer gene in different restorer lines and/or the different genetic backgrounds of different restorer lines. Thus, in order to obtain restorer lines with good restorer capacity, it is desired to have plant-expressible chimeric barstar genes that are expressed at high levels to produce large amounts of barstar in stamen cells, particularly in anther cells, especially in tapetum cells of a plant.

This invention thus provides improved barstar DNAs which, all other things being equal, are more efficiently expressed in plant cells—thereby producing in those cells higher levels of active barstar protein, particularly improved barstar protein—than wild-type barstar DNAs. Thus, improved fertility restorer genes are expressed, in plants of at least one plant species (and preferably in plants of several plant species, particularly several monocot plant species) at a level which is on the average higher than the level observed with similar restorer genes comprising wild-type barstar DNA. An average higher level of expression means that the amount of barstar produced in particular organs (e.g. anthers) of different restorer lines containing the fertility restorer gene of this invention at different genetic loci and/or within different genetic backgrounds is significantly higher than the amount of barstar produced in the stamen of different restorer lines containing similar fertility restorer genes comprising wild-type barstar DNA at different genetic loci and within different genetic background.

Generally the invention provides "improved" barstar coding regions that have a nucleotide sequence containing as a second codon a codon that codes for an amino acid selected from the group of Valine (Val), Alanine (Ala), Aspartic acid (Asp), Glutamic acid (Glu) and Glycine (Gly). It is particularly preferred that this second codon encodes Alanine. These codons start with a G which provides for an optimal translation initiation context at position +4 (i.e. the first nucleotide of the second codon of the barstar coding sequence). Thus the N-terminus of the barstar, encoded by the improved barstar DNA, consists of Met-Xaa in which Xaa is Ala, Val, Gly, Glu, or Asp, and is preferably Ala (more preferably an Ala encoded by a GCC codon). Preferably the improved barstar DNAs encode a barstar comprising the amino acid sequence of SEQ ID No 2 between amino acids residues 3 and 90. Examples of improved barstars DNAs are 1) a barstar DNA encoding a barstar having the sequence of SEQ ID No 2 in which the second amino acid (Lys) is replaced by Xaa as defined above, and 2) a barstar DNA encoding a barstar having the amino acid sequence of SEQ ID No 4. It was found that modifying the N-terminus of the barstar protein in a nonconservative way did not negatively affect the specific biological activity of barstar. In fact genes comprising these improved barstar DNAs, when expressed in plants, particularly when expressed in monocots (such as corn, rice and wheat), generally produced more barstar protein as assessed by Western blotting of stamen tissues. This increase in barstar production in tapetum cells may be due to improved translation but also to improved stability of the barstar protein.

It was also found that modifying a barstar coding sequence to reduce the % AT of this sequence below 40% resulted in an improved barstar DNA that could be used to considerably increase the level of production of protein with barstar activity in plant cells, particularly in tapetum cells. Such improved barstar coding sequences will herein be generally designated as "synthetic" barstar coding sequences.

It is preferred that the synthetic barstar DNAs have a codon usage which is preferred in the majority of plant species in which it is intended to be used, e.g. in restorer lines. A preferred codon usage of a barstar DNA for a majority of N plant species X1, X2, . . . XN means that for each amino acid, for which more than one codon exists, the most frequent codon for that amino acid in the synthetic barstar DNA (the "barstar codon" for that amino acid), preferably every codon for that amino acid, is a codon that in each of more than N/2 plant species has an overall frequency that is 1) at least twice the overall frequency of the least used codon and/or 2) more than half of the overall frequency of the most used codon.

It is also preferred that for at least 17, preferably for at least 18 of the 19 amino acids for which multiple codons exist, the most frequently used codon, preferably every codon, in the synthetic barstar DNA is a codon that in each of the N plant species has an overall frequency that is 1) at least twice the overall frequency of the least used codon and/or 2) more than half of the overall frequency of the most used codon. Example 2 describes the design of a particular synthetic barstar DNA with optimized codon usage with respect to five plant species (N=5) i.e. oilseed rape, cotton, corn, wheat and rice.

For the purpose of this invention the overall codon frequencies for various plant species as published by Ikemura are used (Ikemura, 1993, In "Plant Molecular Biology Labfax", Croy, ed., Bios Scientific Publishers Ltd., pp. 37–48). Preferred plant species in which the synthetic barstar DNAs of this invention are used, e.g. in restorer lines, are oilseed rape, cotton, maize, rice, and wheat, particularly oilseed rape, maize and rice, especially oilseed rape and maize.

The synthetic barstar DNAs are preferably further characterized by having CG dinucleotides and CNG trinucleotides, which are targets for methylation in plant cells, at low frequencies. Thus the synthetic barstar DNAs of this invention are characterized by:

having not more that 7% of CG dinucleotides, preferably having not more than 6% of CG dinucleotides, particularly having between 5.5 and 6% CG dinucleotides (which is about 15 or 16 CG nucleotides in a coding sequence of 270–273 bp), and/or, having not more than 9.5% CNG trinucleotides (where N is any nucleotide), preferably having not more than 9% CNG trinucleotides, particularly having between 8.5 and 9% CNG trinucleotides (which is about 23–25 CNG trinucleotides in a coding sequence of 270–273 bp).

The synthetic barstar DNAs of this invention are further preferably characterized by having no more than 7, preferably no more than 5, particularly no more than 3 tetranucleotides consisting of only one kind of nucleotide (i.e. AAAA, CCCC, GGGG, TTTT) and having no more than 2, preferably no more than 1 pentanucleotide consisting of only one kind of nucleotide (i.e. AAAAA, CCCCC, GGGGG, TTTTT).

Synthetic barstar DNAs of this invention include those coding for wild-type barstar (SEQ ID No 2), e.g. a barstar DNA having the nucleotide sequence of SEQ ID No 3 between positions 7 and 273, preceded by ATG. However, preferred synthetic barstar DNAs of this invention are synthetic barstar coding sequences that encode a barstar having an amino acid sequence starting with Met-Xaa wherein Xaa is Valine, Alanine, Aspartic acid, Glutamic acid or Glycine, and preferably wherein Xaa is Alanine. Preferred synthetic barstar DNAs are DNAs having the nucleotide sequence of SEQ ID No 3 between positions 7 and 273, preceded by ATGGNN, preferably by ATGGCN (where N is any nucleotide). A particularly preferred synthetic barstar DNA is a DNA having the nucleotide sequence of SEQ ID No 3.

Preferably, the synthetic barstar coding sequence and the wild type barstar coding sequence code for barstar proteins having at least 80% sequence identity.

For the purpose of this invention the % sequence identity of two related nucleotide sequences (e.g. two barstar DNAs) or amino acid sequences (i.e. two barstars) refers to the number of positions in the two optimally aligned sequences which have identical residues (×100) divided by the number of positions compared. A gap, i.e. a position in an alignment where a residue is present in one sequence but not in the other is regarded as a position with non-identical residues.

Restorer genes comprising the synthetic barstar DNAs of this invention may be used for producing restorer lines in different plant species but are particularly useful for producing restorer lines in cereals, especially in corn, rice and wheat.

This invention thus also provides improved barstar proteins which have an N-terminus which consists of Met-Xaa (where Xaa is as defined above). Particularly preferred improved barstars of this invention comprise the sequence of SEQ ID No 2 between residues 3 and 90, and are, for example: 1) a barstar having the amino acid sequence of SEQ ID No 4, and 2) a barstar having the amino acid sequence of SEQ ID No. 2 wherein the second amino acid (Lys) is replaced by Xaa as defined above.

Furthermore it goes without saying that the region of these preferred improved barstars that corresponds to the sequence beween residues 3 and 90 of SEQ ID No 2 may be modified, as long as the overall amino acid sequence has at least 80%, preferably at least 85%, particularly at least 90% sequence similarity with SEQ ID No 2, and as long as the improved barstar is capable of inhibiting at least 50%, preferably at least 75%, particularly at least 90% of the activity of secreted barnase under standard conditions.

As indicated above the modification at the N-terminus of a barstar protein (i.e. the introduction of an N-terminus consisting of Met-Xaa- . . . ) is a nonconservative modification, which however does not negatively affect the specific biological activity of the improved barstars of this invention when they are produced in plant cells. This is exemplified for the improved barstar of SEQ ID No 4 in example 6.

This invention thus also provides fertility restorer genes which are characterized in that they contain the improved and/or synthetic barstar DNAs of this invention, and which can be used to produce improved transgenic restorer plants of a plant species, i.e. restorer plants with good restorer capacity. It goes without saying that the barstar DNA in the fertility restorer gene may be translationally fused to other coding sequences so that it will be expressed as part of a fusion protein.

In principle any promoter can be used as a restorer promoter in the fertility restorer gene in the restorer plant of this invention. The only prerequisite is that such restorer plant which contains the fertility-restorer gene, is capable of restoring the fertility to a male-sterile line, i.e. of producing restored plants (comprising both the male-sterility gene and the fertility restorer gene) that are phenotypically normal and male-fertile. This requires that the restorer promoter in the fertility-restorer gene should be at least active in those stamen cells of a plant in which the sterility promoter of the corresponding male-sterility gene can direct expression of the barnase DNA. In this regard it will be preferred that the sterility promoter and the restorer promoter are the same (e.g. both TA29 promoter or both CA55 promoter). However, the sterility promoter may be active only in stamen cells while the restorer promoter is also active in other cells. For instance, the sterility promoter can be a stamen-selective (such as the TA29 or CA55 promoter) while the restorer promoter is a constitutive promoter such as the 35S-tap promoter which is a 35S promoter that is modified to be active in tapetum cells (van der Meer et al, 1992, the Plant Cell 4:253–262).

Of course, the improved restorer DNAs of this invention may also be used for other purposes than restoration of male fertility in plants. In this regard the improved and/or synthetic barstar DNAs of this invention may be used in any circumstance where neutralizing the activity of barnase in plant cells may be useful, such as for example described in EP 0,412,911, WO 93/19188, WO 92/21757, WO 93/25695 and WO 95/02157. For these uses the barstar DNA may be placed under the transcriptional control of other promoters that are more suitable, and promoters like the 35S promoter or the promoter of the nopaline synthase gene of Agrobacterium T-DNA may be used. Minimal promoters (i.e. plant promoters essentially containing only a TATA box without any other regulatory enhancer elements) may also be used and the barstar DNAs of this invention may even be used without any promoter at all (for instance when it is intended that the barstar DNA is transcribed under the control of an endogenous promoter in transformed plant cells).

The fertility restorer gene R as used in the restorer plant preferably also comprises at least a second marker gene which comprises at least:
  1) a second marker DNA encoding a second marker RNA, protein or polypeptide which, when present at least in a specific tissue or specific cells of the plant, renders the plant easily separable from other plants which do not contain the second marker RNA, protein or polypeptide encoded by the second marker DNA at least in the specific tissue or specific cells, and,
  2) a second marker promoter capable of directing expression of the second marker DNA at least in the specific tissue or specific cells: the second marker DNA being in the same transcriptional unit as, and under the control of, the second marker promoter.

Thus a restorer plant of this invention contains a foreign "restorer locus" which contains the restorer gene R comprising the improved restorer DNA of this invention.

The restorer locus preferably also comprises in the same genetic locus at least one second marker gene.

Preferred restorer plants of this invention are monocot restorer plants, preferably corn, rice or wheat plants, that produce, on the average, at least 10 ng, preferably at least 20 ng, particularly at least 40 ng (and up to 100 to 200 ng) barstar per mg total protein extracted from their isolated inflorescences (e.g. panicles in rice and wheat, tassels in corn—see e.g. Example 4).

Especially preferred restorer plants of this invention will produce the improved barstars of this invention, particularly barstar having the amino acid sequence of SEQ ID No. 4.

First and second marker DNAs and first and second marker promoters that can be used in the first and second marker genes of this invention are also well known (EP 0,344,029; EP 0,412,911). In this regard it is preferred that the first and second marker DNA are different, although the first and second marker promoter may be the same.

Foreign DNA such as the fertility-restorer gene, the male-sterility gene, or the first or second marker gene preferably also are provided with suitable 3' transcription regulation sequences and polyadenylation signals, downstream (i.e. 3') from their coding sequence i.e. respectively the fertility-restorer DNA, the male-sterility DNA, or the first or second marker DNA. In this regard foreign transcription 3' end formation and polyadenylation signals suitable for obtaining expression of the chimeric gene can be used. For example, the foreign 3' untranslated ends of genes, such as gene 7 (Velten and Schell (1985) Nucl. Acids Res. 13:6998), the octopine synthase gene (De Greve et al., 1982, J. Mol. Appl. Genet. 1:499; Gielen et al (1983) EMBO J. 3:835; Ingelbrecht et al., 1989, The Plant Cell 1:671) and the nopaline synthase gene of the T-DNA region of *Agrobacterium tumefaciens* Ti-plasmid (De Picker et al., 1982, J. Mol. Appl. Genet. 1:561), or the chalcone synthase gene (Sommer and Saedler, 1986, Mol. Gen. Genet. 202:429–434), or the CaMV 19S/35S transcription unit (Mogen et al., 1990, The Plant Cell 2:1261–1272) can be used.

The fertility-restorer gene, the male-sterility gene, or the first or second marker gene in accordance with the present invention are generally foreign DNAs, preferably foreign chimeric DNA. In this regard "foreign" and "chimeric" with regard to such DNAs have the same meanings as described in EP 0,344,029 and EP 0,412,911.

The cell of a plant, particularly a plant capable of being infected with Agrobacterium such as most dicotyledonous plants (e.g. *Brassica napus*) and some monocotyledonous plants, can be transformed using a vector that is a disarmed Ti-plasmid containing the male-sterility gene or the fertility restorer gene and carried by Agrobacterium. This transformation can be carried out using the procedures described, for example, in EP 0,116,718 and EP 0,270,822. Preferred Ti-plasmid vectors contain the foreign DNA between the border sequences, or at least located to the left of the right border sequence, of the T-DNA of the Ti-plasmid. Of course, other types of vectors can be used to transform the plant cell, using procedures such as direct gene transfer (as described, for example, in EP 0,233,247), pollen mediated transformation (as described, for example, in EP 0,270,356, PCT patent publication "WO" 85/01856, and U.S. Pat. No. 4,684,611), plant RNA virus-mediated transformation (as described, for example, in EP 0,067,553 and U.S. Pat. No. 4,407,956) and liposome-mediated transformation (as described, for example, in U.S. Pat. No. 4,536,475). Cells of monocotyledonous plants such as the major cereals including corn, rice, wheat, barley, and rye, can be transformed (e.g. by electroporation) using wounded or enzyme-degraded intact tissues capable of forming compact embryogenic callus (such as immature embryos in corn), or the embryogenic callus (such as type I callus in corn) obtained thereof, as described in WO 92/09696. In case the plant to be transformed is corn, other recently developed methods can also be used such as, for example, the method described for certain lines of corn by Fromm et al., 1990, Bio/Technology 8:833; Gordon-Kamm et al., 1990, Bio/Technology 2:603 and Gould et al., 1991, Plant Physiol. 95:426. In case the plant to be transformed is rice, recently developed methods can also be used such as, for example, the method described for certain lines of rice by Shimamoto et al., 1989, Nature 338:274; Datta et al., 1990, Bio/Technology 8:736; and Hayashimoto et al., 1990, Plant Physiol. 93:857.

The transformed cell can be regenerated into a mature plant and the resulting transformed plant can be used in a conventional breeding scheme to produce more transformed plants with the same characteristics or to introduce the male-sterility gene, or the fertility-restorer gene in other varieties of the same related plant species. Seeds obtained from the transformed plants contain the chimeric gene(s) of this invention as a stable genomic insert. Thus the male-sterility gene, or the fertility-restorer gene of this invention when introduced into a particular line or variety of a plant species can always be introduced into any other line or variety by backcrossing.

The above-described method for reducing the AT content of a coding DNA while optimizing the codon usage of that coding DNA for a series of of plant species, as used for preparing the synthetic barstar DNAs of this invention, can of course also be applied to any coding sequence for which optimal expression is desired in a number of plant species. In this regard, the method can for example be applied to genes from *Bacillus thuringiensis* that encode insecticidal proteins, such as the full-length and truncated CryIab and Cry9C genes (EP 0,193,259; EP 0,654,075).

Unless otherwise indicated all experimental procedures for manipulating recombinant DNA were carried out by the standardized procedures described in Sambrook et al., 1989, "Molecular Cloning: a Laboratory Manual", Cold Spring Harbor Laboratory, and Ausubel et al, 1994, "Current Protocols in Molecular Biology", John Wiley & Sons.

The polymerase chain reactions ("PCR") were used to clone and/or amplify DNA fragments. PCR with overlap extension was used in order to construct chimeric genes (Horton et al, 1989, Gene 77:61–68; Ho et al, 1989, Gene 77:51–59).

All PCR reactions were performed under conventional conditions using the Vent™ polymerase (Cat. No. 254L—Biolabs New England, Beverley, Mass. 01915, U.S.A.) isolated from *Thermococcus litoralis* (Neuner et al., 1990, Arch. Microbiol. 153:205–207). Oligonucleotides were designed according to known rules as outlined for example by Kramer and Fritz (1987, Methods in Enzymology 154:350), and synthesized by the phosphoramidite method (Beaucage and Caruthers, 1981, Tetrahedron Letters 22:1859) on an applied Biosystems 380A DNA synthesizer (Applied Biosystems B.V., Maarssen, Netherlands).

In the description and in the following examples, reference is made to the following sequence listing and figures:

| Sequence Listing | |
|---|---|
| SEQ ID No 1: | wild type barstar DNA |
| SEQ ID No 2: | wild type barstar |
| SEQ ID No 3: | synthetic barstar DNA |
| SEQ ID No 4: | improved barstar |
| SEQ ID No 5: | plasmid pMV71 |
| SEQ ID No 6: | relevant part of plasmid pLH43 |
| SEQ ID No 7: | T-DNA of plasmid pTTS24 |
| SEQ ID No 8: | oligonucleotide CASOLX1 |
| SEQ ID No 9: | oligonucleotide CASOLX2 |
| SEQ ID No 10: | plasmid pLH48 |

When making reference to nucleotide or amino acid sequences, it should be understood that a sequence between position X and Y (or alternatively a sequence from position X to position Y) is a sequence that includes the residues at position X and Y.

Functional DNA elements are designated using the abbreviations as used in the sequence listing.

EXAMPLES

Example 1
Preparation of an Improved Barstar DNA

An improved barstar DNA was prepared by inserting by site directed mutagenesis the Alanine codon GCC between the first codon (ATG) and the second codon (AAA) of wild-type barstar. The improved barstar DNA thus encodes an improved barstar which, when compared to wild-type barstar has an altered N-terminus which consists of Met-Ala-Lys (instead of Met-Lys in wild-type barstar). This nonconservative modification at the N-terminus does not affect the biological activity of the improved barstar in plant cells (see Example 6).

Example 2
Design and Preparation of a Synthetic Barstar DNA

A synthetic barstar DNA encoding the improved barstar of Example 1 was designed according to the following criteria:
 the percent A and T nucleotides in the synthetic barstar should be below 40% (wild-type barstar DNA has a % AT of 51.6). AT rich genes have a higher likelihood of including polyadenylation signals and intron recognition sequences which can prevent or decrease expression of especially long coding sequences (e.g. Bt coding sequences) in plant cells.
 despite the increase of C and G nucleotides the number of CG dinucleotides and CNG trinucleotides should remain as low as possible. This is because CG dinucleotides and CNG trinucleotides are targets for methylation which can inactivate a gene in plant cells.
 the codon usage should be as optimal as possible in a wide range of plant species, particularly in oilseed rape, cotton, corn, rice and wheat. Therefore for each amino acid a codon (or codons) were selected for predominant use in the barstar DNA that in the majority of plant species has a frequency which is at least more than twice the frequency of the least used codon and/or are at least more than half the frequency of the most used codon. Thus, for each plant species and for each amino acid a list of codons is made which have a frequency which is at least more than twice the frequency of the least used codon in that plant species and/or are at least more than half the frequency of the most used codon in that plant species (codons complying with this criterium are designated as optimal codons for that plant species). The codon that is an optimal codon in the majority of plant species is taken as the predominant codon, preferably the only codon, for that amino acid in the synthetic barstar DNA.
 Conveniently, the frequencies of codons used in this analysis are those listed in Ikemura (supra).
 avoid stretches of longer than 4 identical nucleotides.

A synthetic barstar DNA with the nucleotide sequence of SEQ ID No. 3 was thus obtained This synthetic barstar DNA has an % AT of 38.4, and nevertheless contains only 16 CG dinucleotides and 24 CNG trinucleotides. The synthetic barstar DNA does not contain potential plant polyadenylation signals or intron splice sites. The codon usage of the synthetic barstar DNA appears suitable for expression in at least oilseed rape, cotton, corn rice and wheat (Table 1). For the 18 amino acids for which multiple codons exist 17 amino acids are predominantly encoded (and 16 are exclusively encoded) in the synthetic barstar DNA by a codon which is an optimal codon in each of these five plant species. In fact all the amino acids for which multiple codons exist are predominantly encoded in the synthetic barstar DNA by an optimal codon for at least three of the five species.

The synthetic barstar DNA contains only 1 CCCCC and 1 GGGG stretch.

The synthetic barstar of SEQ ID No 3 allows use of the following unique restriction sites for cloning purposes: NcoI, BspE1 and KasI.

Example 3
Expression of Improved Barstar DNAs in Corn Cells

Cultured Black Mexican Sweet (BMS) corn cells were bombarded with the Bio-Rad PDS-1000/HE particle gun (Bio-Rad, Laboratories, Hercules, Calif., U.S.A.) using microprojectiles (gold particles) coated with either plasmid pLH43 or with plasmid pMV71 as follows.

BMS suspension cells were placed on appropriate filters and bombarded by conventional procedures (Kirihara, 1994, In "The Maize Handbook", Freeling and Walbot, eds., Springer Verlag, pp 690–694), modified by including an osmotic pretreatment (Russel et al, 1992, In Vitro 28:97–105). The gold particles were coated with a mixture of the appropriate plasmid DNA containing the barstar DNA and plasmid pAct1-D (McElroy et al, 1990, The Plant Cell 2:163–171) in a ratio 5:1 using the procedures described in the suppliers manual. pAct1-D is a plasmid containing the gus gene (which encodes beta-glucuronidase) under the control of the promoter of the rice actin gene which has essentially the sequence as disclosed in SEQ ID No 5 from position 1999 to 3400.

For each plasmid two to three filters were bombarded. 24 hours after bombardment, the cells from each filter were collected and ruptured by grinding in liquid nitrogen. The ruptured cells for each filter were divided in two equal amounts, one for a barstar assay and one for a GUS assay.

From one half of the ruptured cells from each bombarded filter, total soluble cellular protein was extracted in extraction buffer (50 mM Tris/HCl pH 7.5, 5% glycerol, 100 mM KCl, 1 mM benzamidin.HCl, 5 mM e-amino-n-caproic acid, 10 mM EDTA, 10 mM EGTA, 1 µg/ml antipain, 1 µg/ml leupeptin, 14 mM beta-mercaptoethanol, 1.5% polyvinylpolypyrrolidone, 1 mM PMSF). Protein concentration was measured by the Bio-Rad Bradford assay. Per sample 50 µg of proteins were loaded on an 18% SDS-polyacrylamide gel and separated by electrophoresis. 0.1, 0.5, 1, 2.5 and 5 ng of purified barstar were loaded on the gel as positive controls.

Proteins were then electroblotted onto Hybond C using TGM-buffer (25 mM Tris pH 8.3, 192 mM glycine, 20% v/v methanol) for 2 hours at 60 V. The filters were then incubated first for 2 hours in 0.5% PBS-Tween 20 and then overnight in a solution of primary antibodies (1/1000 dilution of polyclonal rabbit IgG anti-barstar antibody in PBS-0.5% Tween 20). The filters were then washed four times for 5 minutes in PBS and then incubated for 1 hour in a solution of donkey anti-rabbit-IgG, horseradish peroxidase linked (Amersham, Buckinghamshire, Great Britain) 1/1000 dilution in PBS-0.5% Tween 20). The filters were then again washed four times for 5 minutes. in PBS and proteins were then detected using the ECL detection system (Amersham). The amount of barstar was measured by densitometry scanning of the autoradiographs.

In parallel, activity of beta-glucuronidase in proteins extracted from the other half of ruptured cells from each bombarded filter was measured by a fluorogenic assay Jefferson, 1987, Plant Mol. Biol. Reporter 5:387–405).

Barstar production from a particular plasmid was determined by comparing the amount of barstar per (arbitrary) unit GUS activity.

pMV71 is a plasmid having the nucleotide sequence of SEQ ID No. 5 and contains the improved barstar DNA of Example 1. This variant barstar DNA is operably linked to the rice actin promoter and the 3' untranslated end of the nopaline synthase gene of Agrobacterium T-DNA. pLH43 is a plasmid having the nucleotide sequence of SEQ ID No. 5 in which the sequence between nucleotides 3399 and 4021 is replaced with the nucleotide sequence of SEQ ID No. 6. pLH43 contains the synthetic barstar DNA of Example 2 (SEQ ID No. 3) operably linked to the rice actin promoter and the 3' untranslated end of the nopaline synthase gene of Agrobacterium T-DNA.

pTS410 is a plasmid having the nucleotide sequence of SEQ ID No 5 in which nucleotides 3404 to 3406 (i.e. the second codon of the barstar DNA in pMV71) have been deleted.

The results of the above experiment is presented in Table 2 which shows measurements from individual bombardments. It can easily be seen that the introduction of the improved barstar DNAs of pMV71 and pLH43 result on the average in a significantly higher production of (improved) barstar protein when compared to the production of (wild-type) barstar protein after introduction of the wild-type barstar DNA of pTS410. In addition it can be seen that the introduction of the improved synthetic barstar DNA of pLH43 in corn cells results in a significantly higher production of (improved) barstar protein in those cells when compared to the production of (also improved) barstar protein after introduction of the improved barstar DNA of pMV71.

Example 4
Expression of Improved Barstar DNAs in Rice Plants

Four transgenic male-sterile rice lines of cultivar Kochihibiki were obtained, using plasmid pTS172, essentially as described in WO 92/13956. Plasmid pTS172 contains the following chimeric genes: P35S-bar-3'g7 and PE1-barnase-3'nos and can be obtained from pTS173 (see below) by ligating the large fragment of pTS173, digested with BstEll and MscI to the small BstEII-MscI fragment of pJVR2-E1. These lines were designated as K104, K107, K109 and K111.

Seven transgenic male fertile restorer rice plants of cultivar Chiyonishiki were obtained essentially as described in WO 92/13956 using plasmid pTS173 which contains the following chimeric genes: P35S-bar-3'g7 and PE1-wild-type barstar-3'nos. pTS173 is derived from pJVR3-E1 (WO 92/13956) by replacing the 35S promoter and the 3' untranslated end of the chimeric bar gene of pJVR3-E1 by the 35S promoter and the 3' untranslated end of the chimeric bar gene of pTTS24 as follows. From the T-DNA insert of plasmid pTTS24 (SEQ ID No. 7) a DNA fragment containing the 3' end of T-DNA gene 7 and part of the bar gene is amplified by PCR using the oligonucleotide primers CASOLX1 (SEQ ID No 8), which overlaps the KpnI site in the bar gene, and CASOLX2 (SEQ ID No 9). The PCR product is cleaved with AatII and KpnI, and ligated to the large fragment of plasmid pJVR3-E1 cleaved with AatII and KpnI. From the obtained plasmid the smaller NcoI+NotI fragment, (containing P35S) is replaced by the corresponding NcoI–NotI fragment from pTTS24 (positions 880 to 2281 in SEQ ID No 7), resulting in pTS173.

The resulting lines were designated as C111, C113, C117, C118, C120, C121 and C125. All these plants thus contain the wild type barstar DNA of SEQ ID No 1 under control of the E1 promoter (WO 92/13956).

32 additional restorer plants were obtained using Agrobacterium-mediated transformation of wounded compact embryogenic callus (obtained from rice immature embryos of cultivar Kochihibiki)(WO 92/09696). The Agrobacterium strain used for transformation was strain Ach5 (Genetello et al, 1977, Nature 265:561–563) cured from its wild-type Ti-plasmid and containing plasmids pGV4000 and pTTS24. pTTS24 is an intermediate cloning vector which resembles pGSC1700 (Cornelissen and Vandewiele, 1989, NAR 17:19–29) in its essential characteristics but primarily differs from that plasmid by lacking the beta-lactamase gene and by containing a T-DNA having the nucleotide sequence of SEQ ID No 7. pGV4000 is a disarmed Ti-plasmid which is derived from pMP90 (Koncz and Schell, 1986, Mol. Gen. Genet. 204:383–396) and which contains a region which allows homologous recombination with a corresponding region in pTTS24.

These plants, which all contain the synthetic barstar DNA of Example 2 (SEQ ID No 3) under control of the E1 promoter, were designated with the "OSC" numbers as used in Table 3.

The amount of barstar protein was determined in all restorer lines. Per line one to two immature panicles (i.e. panicles in which the majority of spikelets are approximately 3.5 to 4.5 mm long) of a single plant were crushed in liquid nitrogen. Proteins were extracted and detected as described in Example 3.

The results are summarized in Table 3. It can be seen that the restorer lines containing the barstar DNA of SEQ ID No 3 produce significantly more barstar than those lines that contain the barstar DNA of SEQ ID No 1.

It was confirmed that the amount of barstar mRNA was directly related to the amount of barstar protein in the panicles (data not shown). It was further confirmed that the production of barstar protein is effectively restricted to the flowers of the panicles (data not shown).

Selected restorer lines were crossed with the four male-sterile lines. It was observed that restorer capacity of the restorer lines was correlated with the amount of barstar protein produced in the flowers. Lines producing between 4 and 10 ng barstar per mg of extracted protein were observed to be able to partially restore microspore development to male-sterile lines in the sense that the "restored plants" produced nonviable pollen (male-sterile plants do not produce pollen at all). It was observed that restorer lines producing 50 ng or more barstar per mg of extracted protein were able to fully restore the fertility to all tested male-sterile lines, i.e. all restored progeny plants produced fully viable and functional pollen, and normal seedset after self-pollination.

Selected restorer lines were also self-pollinated and immature panicles were harvested from the transgenic progeny plants. The expression level, as determined by the amount of barstar produced, was at least equal to, and in many plants greater than, that determined in the primary transformants. Generally, these observations confirm that barstar expression level is stably transmitted to progeny plants.

Example 5
Expression of Improved Barstar DNAs in Corn Plants.

A transgenic male-sterile corn line, designated as MS3, was obtained essentially as described in WO 92/13956 using plasmid pVE108.

Several transgenic male fertile restorer corn plants, containing the wild-type barstar DNA of SEQ ID No 1 under the control of either the TA29 promoter (EP 344,029) or the CA55 promoter (WO 92/13957) were obtained essentially as described in WO 95/34634. In particular seven restorer lines were obtained by transformation of corn with plasmids pCOL100 and pDE110 (WO 92/34634) which contains inter alia the TA29 promoter operably linked to the barstar DNA as described in SEQ ID No 1. When crossed to MS3 plants, restoration was incomplete in that maximally 75% of the anthers produced viable pollen (this shows that the MS3 line is especially difficult to restore as good restoration was obtained with other male sterile lines—data not shown).

Similarly, six transgenic restorer corn lines were obtained by transformation of corn with plasmid pLH48 (together with plasmids selected from pCOL9S or PLH52 or p35S-Bperu or pCOL11 (WO 92/34634)). These restorer lines all contain at least the synthetic barstar DNA of Example 2 (SEQ ID No 3) under control of the TA29 promoter. The six restorer lines were crossed to MS3 plants and for four restorer lines complete restoration was observed. One of these four restorer lines was designated as RZM583-0101.

The transgenic line MS3 was pollinated by transgenic line RZM583-0101, and progeny plants containing both the chimeric barnase gene and the chimeric barstar gene were identified by PCR screening. Those fertility restored progeny plants were used to pollinate silks of MS3 plants. Among 90 progeny plants of this last cross, 15 plants were identified (by quantitative Southern blotting) to be homozygous for the chimeric barnase gene of MS3. Among those, plants that did not contain the chimeric barstar gene of RZM583-0101 were male-sterile, while those plants that contained the chimeric barstar gene of RZM583-0101 were fully male fertile. This demonstrates that fertility of plants containing a chimeric barnase gene in homozygous condition can be fully restored by a chimeric barstar gene comprising the improved synthetic barstar DNA.

Thus it can be concluded that the restorer lines containing the improved synthetic barstar DNA have a significantly better restorer capacity.

The amount of barstar in immature tassels (comprising microspores in the uninucleate stage) of progeny restorer plants was determined essentially as described in Example 3. It was observed that the amount of barstar protein was significantly higher in the tassels of restorer plants containing the improved synthetic barstar DNA than in those containing the wild-type barstar DNA. For example in a plant containing the wild-type barstar DNA, the amount of barstar protein was determined to be below 20 ng barstar/mg total protein. In contrast in two lines containing the improved synthetic barstar DNA the amount of barstar protein in immature tassels was determined to be respectively 210 and 100 ng barstar/mg total protein.

Example 6
Activity of Wild Type Barstar and Improved Barstar when Produced in Stamen Cells of Oilseed Rape.

Oilseed rape plants (cv. Drakkar) were transformed using Agrobacterium-mediated transformation, with plasmids pTHW118 or pTTS139. Plasmid pTHW118 contains the wild-type barstar DNA (SEQ ID No 1) under the control of the TA29 promoter. Plasmid pTTS139 contains an improved barstar DNA containing an additional GCC alanine codon between the first and second codon of wild-type barstar DNA. Thus the barstar DNA in pTTS139 encodes the improved barstar protein of SEQ ID No 4.

Two oilseed rape lines transformed with pTHW118, respectively designated as DBN366-0011 and DBN366-0029, and two oilseed rape lines transformed with pTTS139, respectively designated as DBN342-1010 and DBN367-0035 were selected for quantitative analysis.

Oilseed rape flower buds with a length of about 3 to 4 mm were isolated from the plants and were crushed in liquid nitrogen. Proteins were extracted, and the amount of total extracted protein, as well as the amount of barstar detectable by Western blot, was determined, all essentially as described in Example 3. Table 4 presents the amount of total extractable protein (column 4) and the amount of barstar (column 2) found in each line.

Barstar activity was assayed essentially as described in Fitzgerald and Hartley (1993, supra). To 600 µl TE buffer (10 mM Tris/HCl pH 8.0; 1 mM EDTA) was added 20 µl of a 0.02 M NH4 acetate pH 8.0 solution containing 10 µg/ml bovine serum albumin and 0.1 µg/ml barnase, "x" µl of a 1 in 5 dilution of proteins extracted from the flower buds ("Y" is 0, 4, 8, 12, 16, 20 respectively).

After mixing and waiting for about 1 minute, 6 µl of a 1 in 10 dilution of a stock solution containing 0.4 mg/ml polyethenoadenosinephosphate in TE buffer was added.

The final solution was mixed and transferred immediately to a cuvette and the increase in fluorescence was recorded for one to two minutes.

The values of the initial increase in fluorescence/minute was plotted against "x" (the volume of barstar containing solution). In each case a linear relationship was obtained, as expected. The intercept of the regression line with the X-axis was calculated (Table 4, column 3): this represents the volume of "x" which contains sufficient barstar to completely neutralize 2 ng of barnase (i.e. the volume containing a molar amount of barstar which is equivalent with 2 ng barnase). From this the amount of "active" barstar in the flower buds (Table 4, column 5), as well as the proportion of "active" barstar to total barstar protein detected by Western blot (Table 4, column 6)), can be determined.

From these ratios it can be deduced that the activity of improved barstar is at least equivalent with that of wild-type barstar. However, in lines transformed with pTHW118 (expressing wild type barstar) the average ratio is 0.27 (standard deviation 0.08), while in lines transformed with pTTS139 the average ratio is 0.39 (standard deviation 0.08). The difference between the average ratios for the two types of lines is statistically significant (t=−26, p<0.005). From this it can be concluded that improved barstar, when produced in oilseed rape flower buds will generally result in a higher level of active barstar as compared to wild type barstar.

All publications cited in this application are hereby incorporated by reference.

TABLE 1

| Amino Acid[b] | Barstar codon[c] | Nr[d] | Plant[a] | | | | |
|---|---|---|---|---|---|---|---|
| | | | Oilseed rape | Cotton | Maize | Rice | Wheat |
| Leu | CTC | 9 | + | + | + | + | + |
| | CTT | 2 | + | + | + | + | + |
| | TTG | 1 | + | + | + | + | + |
| Ser | AGC | 4 | + | + | + | + | + |
| | TCC | 1 | + | + | + | + | + |
| Arg | AGG | 3 | + | + | + | + | + |
| Thr | ACC | 4 | + | + | + | + | + |
| Pro | CCC | 1 | + | − | + | + | − |
| | CCG | 1 | + | − | + | + | − |
| Ala | GCC | 6 | + | + | + | + | + |
| | GCT | 1 | + | + | + | + | + |

TABLE 1-continued

| Amino Acid[b] | Barstar codon[c] | Nr[d] | Plant[a] Oilseed rape | Cotton | Maize | Rice | Wheat |
|---|---|---|---|---|---|---|---|
| Gly | GGC | 3 | – | + | + | + | + |
|  | GGT | 1 | + | + | – | – | – |
|  | GGG | 1 | + | + | – | – | + |
| Val | GTG | 4 | + | + | + | + | + |
|  | GTC | 1 | + | + | + | + | + |
| Lys | AAG | 6 | + | + | + | + | + |
| Asn | AAC | 3 | + | + | + | + | + |
| Gln | CAG | 5 | + | + | + | + | + |
|  | CAA | 1 | + | + | + | + | + |
| His | CAC | 1 | + | + | + | + | + |
| Glu | GAG | 11 | + | + | + | + | + |
| Asp | GAC | 4 | + | + | + | + | + |
| Tyr | TAC | 3 | + | + | + | + | + |
| Cys | TGC | 2 | + | + | + | + | + |
| Phe | TTC | 2 | + | + | + | + | + |
| Ile | ATC | 6 | + | + | + | + | + |

[a]+: indicates that, in the selected plant, the codon is an optimal codon in that plant i.e. is a codon that has in that plant a frequency which is at least twice the frequency of the least frequent codon in that plant and/or which is at least 50% of the frequency of the most used codon in that plant. Frequency of codons in the plant species are those listed (in per thousand) by Ikemura (supra)
–: indicates that, in the selected plant, the codon is not an optimal codon in that plant as defined above
[b]amino acid for which multiple codons exist (not Trp, Met)
[c]codon used in the synthetic barstar DNA of SEQ ID No 3 for the amino acid
[d]number of amino acids encoded by this codon in SEQ ID No. 3

TABLE 2

| plasmid | Filter Nr | ng barstar protein[a] | Gus activity[b] | corrected barstar[c] | Mean | SD |
|---|---|---|---|---|---|---|
| pLH43 | 1 | 2.8 | 0.6 | 4.7 | 5.4 | 0.8 |
|  | 2 | 3.7 | 0.6 | 6.2 |  |  |
|  | 3 | 2.7 | 0.5 | 5.4 |  |  |
| pMV71 | 1 | 2.4 | 0.8 | 3.0 | 2.7 | 0.4 |
|  | 2 | 3.6 | 1.3 | 2.8 |  |  |
|  | 3 | 1.1 | 0.5 | 2.2 |  |  |
| pTS410 | 1 | 0.6 | 0.8 | 0.8 | 0.9 | 0.1 |
|  | 2 | 0.8 | 0.8 | 1.0 |  |  |

[a]Amount of barstar/50 µg loaded protein as determined by Western blot
[b]Gus activity is in arbitrary units.
[c]Corrected barstar: ng barstar/units of GUS activity.

TABLE 3

| Nr | Plasmid | Line | ng barstar/mg total protein |
|---|---|---|---|
| 1 | pTS173 | C111 | <2[a] |
| 2 |  | C113 | 4 |
| 3 |  | C117 | <2[a] |
| 4 |  | C118 | 2 |
| 5 |  | C120 | 6 |
| 6 |  | C121 | 2 |
| 7 |  | C125 | 4 |
| 8 | pTTS24 | OSC1156 | 21 |
| 9 |  | OSC1160 | 36 |
| 10 |  | OSC1178 | <12[a] |
| 11 |  | OSC1181 | 39 |
| 12 |  | OSC1185 | <12[a] |
| 13 |  | OSC1187 | 29 |
| 14 |  | OSC1188 | 78 |
| 15 |  | OSC1208 | 22 |
| 16 |  | OSC1210 | <12[a] |
| 17 |  | OSC1212 | 69 |
| 18 |  | OSC1219 | 72 |
| 19 |  | OSC1226 | <12[a] |
| 20 |  | OSC1229 | 42 |
| 21 |  | OSC1235 | <12[a] |
| 22 |  | OSC1237 | 20 |
| 23 |  | OSC1239 | 26 |
| 24 |  | OSC1241 | <12[a] |
| 25 |  | OSC1242 | 43 |
| 26 |  | OSC1247 | 84 |
| 27 |  | OSC1249 | 42 |
| 28 |  | OSC1251 | 65 |
| 29 |  | OSC1254 | 185 |
| 30 |  | OSC1258 | 53 |
| 31 |  | OSC1268 | 130 |
| 32 |  | OSC1271 | 75 |
| 33 |  | OSC1272 | 30 |
| 34 |  | OSC1274 | 138 |
| 35 |  | OSC1276 | <12[a] |
| 36 |  | OSC1278 | 86 |
| 37 |  | OSC1287 | 26 |
| 38 |  | OSC1288 | 32 |
| 39 |  | OSC1293 | <12[a] |

[a]below detection limit

TABLE 4

| Sample | ng b*/mg total protein[1] | X[2] | Total protein (µg/µl)[3] | ng active b*/mg total protein[4] | active b*/total b*[5] |
|---|---|---|---|---|---|
| DBN366-0011 | 300 | 15.3 | 5.4 | 99 | 0.33 |
| DBN366-0029 | 310 | 18.5 | 6.8 | 65 | 0.21 |
| DBN342-1010 | 170 | 23.6 | 4.7 | 74 | 0.44 |
| DBN367-0035 | 280 | 18.4 | 4.8 | 93 | 0.33 |

[1]as determined by Western blot
[2]X-intercept
[3]total amount of protein extracted from flower buds (this is diluted 1 in 5 for barstar activity assay)
[4]estimated amount of active barstar (about 16.36 ng/ml barstar is equimolar with 20 ng/ml barnase)
[5]ratio of active barstar (see 4) above) to total barstar (see 1) above)

What is claimed is:

1. A DNA comprising a barstar DNA encoding a barstar with an amino acid sequence that starts MET-Ala.

2. The DNA of claim 1, wherein said barstar DNA encodes a barstar having the amino acid sequence of SEQ ID No. 4.

3. The DNA of claim 2, wherein said barstar DNA has the nucleotide sequence of SEQ ID No. 3.

4. The DNA of claim 2, wherein said barstar DNA has the nucleotide sequence ATGGCC followed by the nucleotide sequence of SEQ ID No. 1 between position 7 and 270.

5. The DNA of claim 1, wherein said barstar DNA contains less than 40% A and T nucleotides.

6. The DNA of claim 1, which has a codon usage that is optimized for oilseed rape, cotton, maize, rice and wheat.

7. The DNA of claim 1, wherein said barstar DNA contains no more than 7% CG dinucleotides and contains no more than 9.5% of CNG trinucleotides.

8. The DNA of claim 1, wherein said barstar DNA is operably linked to a promoter that directs transcription in plant cells.

9. The DNA of claim 8, wherein said promoter is a promoter that directs transcription selectively in stamen cells of a plant.

10. The DNA of claim 9, wherein said promoter is a promoter that directs transcription at least in tapetum cells of a plant.

11. The DNA of claim 10, wherein said promoter is the promoter of the TA29 gene of tobacco, the promoter of the CA55 gene of corn or the promoter of the E1, the T72 or the T42 gene of rice.

12. The DNA of claim 8, wherein said promoter is a constitutive promoter.

13. The DNA of claim 12, wherein said promoter is the 35S promoter.

14. A plant cell comprising the DNA of any one of claims 1 to 13.

15. The plant cell of claim 14 which also comprises a barnase DNA.

16. A plant comprising the DNA of any one of claims 1 to 13.

17. The plant of claim 16, which also comprises a barnase DNA.

18. The plant of claim 16, which is oilseed rape, cotton, maize, rice or a wheat plant.

19. The plant of claim 16, which is a monocotyledonous plant.

20. The plant of claim 19, which produces at least 20 ng barstar per mg total protein extractable from its inflorescences.

21. A process to restore fertility to a male-sterile plant line, said process comprising the steps of:
 (a) introducing a chimeric gene comprising the DNA of any one claims 8–13, operably linked to a plant-expressible promoter into a plant line;
 (b) crossing said plant line with a male-sterile line which is male-sterile due to the expression of a male-sterility DNA coding for a barnase; and
 (c) obtaining progeny from said male-sterile line comprising said chimeric gene in which fertility is restored.

* * * * *